(12) United States Patent
Chen et al.

(10) Patent No.: US 12,295,412 B2
(45) Date of Patent: May 13, 2025

(54) ORAL POUCH PRODUCT

(71) Applicant: Altria Client Services LLC, Richmond, VA (US)

(72) Inventors: Baiwei Chen, Richmond, VA (US); Feng Gao, Midlothian, VA (US); Shannon M. Black, Richmond, VA (US); Shaoyong Yu, Glen Allen, VA (US); Shuzhong Zhuang, Glen Allen, VA (US); Benjamin L. Ragland, Richmond, VA (US); Rebecca M. Gray, Richmond, VA (US); Fadi Aldeek, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 294 days.

(21) Appl. No.: 17/586,959

(22) Filed: Jan. 28, 2022

(65) Prior Publication Data
US 2023/0240359 A1    Aug. 3, 2023

(51) Int. Cl.
*A24F 23/02* (2006.01)
*A24B 15/30* (2006.01)
*A61K 9/00* (2006.01)
*A61K 31/465* (2006.01)

(52) U.S. Cl.
CPC .............. *A24F 23/02* (2013.01); *A24B 15/30* (2013.01); *A61K 9/009* (2013.01); *A61K 31/465* (2013.01)

(58) Field of Classification Search
None
See application file for complete search history.

(56) References Cited

U.S. PATENT DOCUMENTS

| | | | |
|---|---|---|---|
| 1,771,982 | A | 7/1930 | Mustin |
| 3,303,796 | A | 2/1967 | Novissimo |
| 3,845,217 | A | 10/1974 | Ferno et al. |
| D267,920 | S | 2/1983 | Batts et al. |
| 4,388,328 | A | 6/1983 | Glass |
| D269,712 | S | 7/1983 | Tovey |

(Continued)

FOREIGN PATENT DOCUMENTS

| | | | |
|---|---|---|---|
| AU | 2013/219211 | A1 | 9/2013 |
| CA | 2109895 | A1 | 5/1995 |

(Continued)

OTHER PUBLICATIONS

Pharmaexcipients, Avicel PH 302, Product description. https://www.pharmaexcipients.com/product/avicel-ph-302/#.*

(Continued)

*Primary Examiner* — Michael H. Wilson
*Assistant Examiner* — Michael T Fulton
(74) *Attorney, Agent, or Firm* — Harness, Dickey & Pierce, P.L.C.

(57) ABSTRACT

An oral pouch product includes a wrapper and a filling material. The wrapper defines a cavity. The filling material is in the cavity. The filling material includes a dry mixture and a liquid mixture. The dry mixture includes a cellulosic material and a water-soluble filler. The liquid mixture includes an oil and liquid nicotine. The oil includes a triglyceride, a diglyceride, a monoglyceride, or any combination thereof. The liquid nicotine is dissolved in the oil. The filling material is free of water or includes water in an amount less than or equal to 5 weight percent.

40 Claims, 9 Drawing Sheets

(56) References Cited

U.S. PATENT DOCUMENTS

| | | |
|---|---|---|
| D269,719 S | 7/1983 | Tovey |
| D269,722 S | 7/1983 | Tovey |
| D269,723 S | 7/1983 | Tovey |
| 4,518,615 A | 5/1985 | Cherukuri et al. |
| D285,363 S | 8/1986 | Tovey |
| D286,085 S | 10/1986 | Tovey |
| D296,018 S | 5/1988 | McDonald |
| D296,208 S | 6/1988 | Yang |
| D300,878 S | 4/1989 | Contractor |
| D300,879 S | 4/1989 | Mercer |
| D301,765 S | 6/1989 | Contractor et al. |
| D301,766 S | 6/1989 | Contractor et al. |
| D309,506 S | 7/1990 | Shurkus |
| 4,972,855 A | 11/1990 | Kuriyama et al. |
| 4,981,698 A | 1/1991 | Cherukuri et al. |
| 4,986,286 A | 1/1991 | Roberts et al. |
| D314,442 S | 2/1991 | Shott et al. |
| 5,043,169 A | 8/1991 | Cherukuri et al. |
| 5,064,658 A | 11/1991 | Cherukuri et al. |
| D323,236 S | 1/1992 | Copp |
| D323,388 S | 1/1992 | Becker |
| 5,148,819 A | 9/1992 | Fagg |
| D334,645 S | 4/1993 | Kennedy |
| D343,269 S | 1/1994 | Kirkham |
| 5,284,163 A | 2/1994 | Knudsen et al. |
| D354,806 S | 1/1995 | Tovey |
| 5,435,325 A | 7/1995 | Clapp et al. |
| 5,487,902 A | 1/1996 | Andersen et al. |
| D375,157 S | 10/1996 | Kramer et al. |
| 5,709,895 A | 1/1998 | Tanaka et al. |
| 5,733,587 A | 3/1998 | Ream et al. |
| 5,955,098 A | 9/1999 | Dugger, III |
| D431,863 S | 10/2000 | Richardson |
| D437,671 S | 2/2001 | Fajerstein |
| D441,189 S | 5/2001 | Vazquez |
| D445,236 S | 7/2001 | Kirchner et al. |
| D450,883 S | 11/2001 | Buter et al. |
| 6,344,222 B1 | 2/2002 | Cherukuri et al. |
| 6,350,480 B1 | 2/2002 | Urnezis et al. |
| 6,376,677 B1 | 4/2002 | Chuck et al. |
| D487,755 S | 3/2004 | Kasperik et al. |
| D510,173 S | 10/2005 | Richey et al. |
| D510,174 S | 10/2005 | Richey et al. |
| D516,670 S | 3/2006 | Aselton |
| D535,741 S | 1/2007 | Stawski et al. |
| D539,007 S | 3/2007 | Clark et al. |
| D554,309 S | 10/2007 | Wolk et al. |
| D556,946 S | 12/2007 | Seum et al. |
| D556,947 S | 12/2007 | Seum et al. |
| D580,547 S | 11/2008 | Lolis et al. |
| D591,476 S | 5/2009 | Colman et al. |
| D595,478 S | 7/2009 | Colman et al. |
| D596,738 S | 7/2009 | Chen et al. |
| D599,077 S | 9/2009 | Garcia Aleman et al. |
| D608,976 S | 2/2010 | Colman et al. |
| D626,716 S | 11/2010 | Mederer |
| D685,081 S | 6/2013 | Ferguson et al. |
| 8,469,036 B2 | 6/2013 | Williams et al. |
| D687,207 S | 8/2013 | Kerr et al. |
| 8,501,164 B2 | 8/2013 | Chen |
| 8,545,870 B2 | 10/2013 | Dupinay et al. |
| 8,597,703 B2 | 12/2013 | Boghani et al. |
| 8,741,348 B2 | 6/2014 | Hansson et al. |
| 8,765,178 B2 | 7/2014 | Parikh et al. |
| 8,833,378 B2 | 9/2014 | Axelsson et al. |
| D715,022 S | 10/2014 | Torres Sanchez et al. |
| D715,023 S | 10/2014 | Torres Sanchez et al. |
| D715,024 S | 10/2014 | Torres Sanchez et al. |
| D715,025 S | 10/2014 | Torres Sanchez et al. |
| D715,026 S | 10/2014 | Torres Sanchez et al. |
| 8,940,772 B2 | 1/2015 | Chen |
| D724,778 S | 3/2015 | Hulan |
| 8,978,661 B2 | 3/2015 | Atchley et al. |
| 8,992,974 B2 | 3/2015 | McCarty |
| 9,028,803 B2 | 5/2015 | Nielsen et al. |
| 9,039,839 B2 | 5/2015 | Beeson et al. |
| D731,741 S | 6/2015 | Brown et al. |
| D732,792 S | 6/2015 | Alvarez et al. |
| 9,044,037 B2 | 6/2015 | Ream et al. |
| 9,044,049 B2 | 6/2015 | Winterson et al. |
| 9,066,540 B2 | 6/2015 | Atchley et al. |
| 9,084,439 B2 | 7/2015 | Holton, Jr. |
| D736,369 S | 8/2015 | Bruining et al. |
| D739,516 S | 9/2015 | Hulan |
| D740,928 S | 10/2015 | Bruining et al. |
| 9,155,321 B2 | 10/2015 | Cantrell et al. |
| 9,161,908 B2 | 10/2015 | Nilsson |
| 9,185,931 B2 | 11/2015 | Gao et al. |
| D745,659 S | 12/2015 | Bruining et al. |
| D746,541 S | 1/2016 | Sambashivan |
| 9,283,191 B2 | 3/2016 | Andersen et al. |
| 9,345,267 B2 | 5/2016 | Torrence et al. |
| 9,351,936 B2 | 5/2016 | Gao et al. |
| 9,375,033 B2 | 6/2016 | Lampe et al. |
| D760,991 S | 7/2016 | Ajmera et al. |
| 9,402,809 B2 | 8/2016 | Axelsson et al. |
| 9,402,810 B2 | 8/2016 | Nilsson |
| 9,414,624 B2 | 8/2016 | Carroll et al. |
| 9,420,827 B2 | 8/2016 | Mishra et al. |
| 9,462,827 B2 | 10/2016 | Carroll et al. |
| 9,474,303 B2 | 10/2016 | Holton, Jr. |
| D771,348 S | 11/2016 | Traynor |
| 9,521,864 B2 | 12/2016 | Gao et al. |
| D783,225 S | 4/2017 | D'Agostino |
| 9,629,392 B2 | 4/2017 | Holton, Jr. |
| 9,629,832 B2 | 4/2017 | Hansson et al. |
| 9,693,528 B1 | 7/2017 | Faue et al. |
| 9,693,582 B2 | 7/2017 | Carroll et al. |
| 9,763,928 B2 | 9/2017 | Duggins et al. |
| D798,526 S | 10/2017 | Vielot |
| D802,250 S | 11/2017 | Brunner et al. |
| D802,880 S | 11/2017 | Mathew et al. |
| D805,728 S | 12/2017 | Belt et al. |
| 9,854,831 B2 | 1/2018 | Gao et al. |
| 9,901,113 B2 | 2/2018 | Holton, Jr. |
| 9,907,748 B2 | 3/2018 | Borschke et al. |
| 9,930,909 B2 | 4/2018 | Gao et al. |
| 9,993,020 B2 | 6/2018 | Cantrell et al. |
| 10,039,309 B2 | 8/2018 | Carroll et al. |
| 10,045,976 B2 | 8/2018 | Fusco et al. |
| 10,098,376 B2 | 10/2018 | Strickland et al. |
| 10,105,320 B2 | 10/2018 | Gao et al. |
| D834,781 S | 12/2018 | Traynor |
| 10,172,810 B2 | 1/2019 | McCarty |
| D839,530 S | 2/2019 | Brunner et al. |
| 10,219,999 B2 | 3/2019 | Axelsson et al. |
| 10,244,786 B2 | 4/2019 | Gao et al. |
| 10,244,787 B2 | 4/2019 | Mishra et al. |
| D851,744 S | 6/2019 | Huang et al. |
| 10,349,672 B2 | 7/2019 | Gao et al. |
| 10,357,054 B2 | 7/2019 | Marshall et al. |
| D855,931 S | 8/2019 | Bindra et al. |
| 10,399,712 B2 | 9/2019 | Longest, Jr. et al. |
| 10,413,512 B2 | 9/2019 | Roehrich |
| 10,426,726 B2 | 10/2019 | Neergaard |
| 10,448,669 B2 | 10/2019 | Atchley et al. |
| 10,463,070 B2 | 11/2019 | Carroll et al. |
| 10,485,247 B2 | 11/2019 | Neergaard |
| 10,517,818 B2 | 12/2019 | Jackson et al. |
| 10,537,132 B2 | 1/2020 | Hunt et al. |
| 10,543,205 B2 | 1/2020 | Wittorff et al. |
| 10,561,731 B2 | 2/2020 | Zumpano |
| 10,568,355 B2 | 2/2020 | Marshall et al. |
| 10,611,043 B2 | 4/2020 | Miller et al. |
| 10,617,143 B2 | 4/2020 | Holton, Jr. |
| 10,632,076 B2 | 4/2020 | Wittorff |
| D885,630 S | 5/2020 | Lin |
| D885,706 S | 6/2020 | Bindra et al. |
| D885,707 S | 6/2020 | Bindra et al. |
| 10,702,516 B2 | 7/2020 | Gao et al. |
| 10,736,350 B2 | 8/2020 | Kindvall et al. |
| 10,744,694 B2 | 8/2020 | Miller et al. |
| 10,772,350 B2 | 9/2020 | Cantrell et al. |
| 10,780,085 B2 | 9/2020 | Gao et al. |

(56) References Cited

U.S. PATENT DOCUMENTS

| | | | |
|---|---|---|---|
| 10,834,960 B2 | 11/2020 | Mishra et al. |
| D907,326 S | 1/2021 | Bindra et al. |
| 10,881,132 B2 | 1/2021 | Mua et al. |
| 10,925,309 B2 | 2/2021 | Gao et al. |
| 10,952,461 B2 | 3/2021 | Holton, Jr. |
| 10,980,271 B2 | 4/2021 | Marshall et al. |
| 11,052,047 B2 | 7/2021 | Wittorff |
| 11,058,633 B2 | 7/2021 | Wittorff |
| 11,058,641 B2 | 7/2021 | Wittorff |
| 11,076,631 B2 | 8/2021 | Gao et al. |
| 11,090,263 B2 | 8/2021 | Wittorff |
| 11,096,412 B2 | 8/2021 | Stahl et al. |
| 11,096,895 B2 | 8/2021 | Wittorff |
| 11,096,896 B2 | 8/2021 | Wittorff |
| 11,116,237 B2 | 9/2021 | Cantrell et al. |
| 11,116,758 B2 | 9/2021 | Gao et al. |
| 11,129,792 B2 | 9/2021 | Axelsson et al. |
| 11,129,898 B2 | 9/2021 | Holton, Jr. et al. |
| 2001/0016593 A1 | 8/2001 | Wilhelmsen |
| 2001/0026788 A1 | 10/2001 | Piskorz |
| 2003/0099740 A1 | 5/2003 | Colle et al. |
| 2004/0002520 A1 | 1/2004 | Soderlund et al. |
| 2004/0014680 A1 | 1/2004 | Nakagami et al. |
| 2004/0037879 A1 | 2/2004 | Adusumilli et al. |
| 2004/0101543 A1 | 5/2004 | Liu et al. |
| 2005/0034738 A1 | 2/2005 | Whalen |
| 2005/0053665 A1 | 3/2005 | Ek et al. |
| 2006/0112965 A1 | 6/2006 | Whalen |
| 2007/0062549 A1 | 3/2007 | Holton et al. |
| 2007/0144544 A1 | 6/2007 | Cai et al. |
| 2007/0269386 A1 | 11/2007 | Steen et al. |
| 2008/0286340 A1 | 11/2008 | Andersson et al. |
| 2009/0029018 A1 | 1/2009 | Elejalde et al. |
| 2009/0169677 A1 | 7/2009 | Wittorff et al. |
| 2010/0004294 A1 | 1/2010 | Axelsson et al. |
| 2010/0080847 A1 | 4/2010 | Nakagami et al. |
| 2010/0247586 A1 | 9/2010 | Hugerth et al. |
| 2010/0260690 A1 | 10/2010 | Kristensen et al. |
| 2011/0052756 A1 | 3/2011 | Cervenka et al. |
| 2011/0165253 A1 | 7/2011 | Roehrich |
| 2012/0017924 A1 | 1/2012 | Lindell et al. |
| 2012/0042886 A1 | 2/2012 | Piskorz |
| 2013/0078307 A1 | 3/2013 | Holton, Jr. et al. |
| 2013/0206150 A1 | 8/2013 | Duggins et al. |
| 2013/0309292 A1 | 11/2013 | Andersen |
| 2014/0130813 A1 | 5/2014 | Strehle |
| 2014/0242214 A1 | 8/2014 | Boghani et al. |
| 2015/0050497 A1 | 2/2015 | Gerritzen et al. |
| 2015/0080442 A1 | 3/2015 | McCarty |
| 2015/0096573 A1 | 4/2015 | Gao et al. |
| 2015/0096574 A1 | 4/2015 | Gao et al. |
| 2015/0096575 A1 | 4/2015 | Gao et al. |
| 2015/0096576 A1 | 4/2015 | Gao et al. |
| 2015/0098996 A1 | 4/2015 | Gao et al. |
| 2015/0105431 A1 | 4/2015 | Chen |
| 2015/0174116 A1 | 6/2015 | Mccarty |
| 2015/0225151 A1* | 8/2015 | Osborn ................ A61K 31/465 428/483 |
| 2015/0283070 A1 | 10/2015 | Stenzler et al. |
| 2017/0020812 A1 | 1/2017 | Neergaard |
| 2017/0071929 A1 | 3/2017 | Stenzler et al. |
| 2017/0164651 A1 | 6/2017 | Mua et al. |
| 2017/0172927 A1 | 6/2017 | Fusco et al. |
| 2017/0172995 A1 | 6/2017 | Repaka et al. |
| 2017/0179610 A1 | 6/2017 | Watson |
| 2017/0223800 A1 | 8/2017 | Wu et al. |
| 2017/0258107 A1 | 9/2017 | Miladinov et al. |
| 2017/0280764 A1 | 10/2017 | Sahlen et al. |
| 2017/0311642 A1 | 11/2017 | Cao et al. |
| 2017/0326138 A1 | 11/2017 | Borschke |
| 2017/0360767 A1 | 12/2017 | Duggins et al. |
| 2018/0008562 A1 | 1/2018 | Pulford |
| 2018/0057229 A1 | 3/2018 | St. Lawrence |
| 2018/0140007 A1 | 5/2018 | Aspgren et al. |
| 2018/0140521 A1 | 5/2018 | Geonnotti et al. |
| 2018/0192697 A1 | 7/2018 | Goode |
| 2018/0271139 A1 | 9/2018 | Aspgren et al. |
| 2018/0369225 A1 | 12/2018 | Zuber |
| 2019/0021382 A1 | 1/2019 | Mo et al. |
| 2019/0059438 A1 | 2/2019 | Mishra et al. |
| 2019/0117567 A1 | 4/2019 | Volpe |
| 2019/0117779 A1 | 4/2019 | Holton, Jr. et al. |
| 2019/0174812 A1 | 6/2019 | Nielsen et al. |
| 2019/0200667 A1 | 7/2019 | Phililps et al. |
| 2019/0313689 A1 | 10/2019 | Beeson et al. |
| 2019/0321793 A1 | 10/2019 | Miller |
| 2019/0350858 A1 | 11/2019 | Wittorff |
| 2019/0365672 A1 | 12/2019 | McCarty |
| 2020/0029615 A1 | 1/2020 | Gao et al. |
| 2020/0078349 A1 | 3/2020 | Wittorff et al. |
| 2020/0128870 A1 | 4/2020 | Hassler et al. |
| 2020/0138706 A1 | 5/2020 | Rudraraju et al. |
| 2020/0260775 A1 | 8/2020 | Holton, Jr. |
| 2020/0275689 A1 | 9/2020 | Lewerenz |
| 2020/0297026 A1 | 9/2020 | Kannisto et al. |
| 2020/0297715 A1 | 9/2020 | Gao et al. |
| 2020/0367551 A1 | 11/2020 | Cantrell et al. |
| 2020/0383373 A1* | 12/2020 | Stahl ................ A24B 15/303 |
| 2021/0000158 A1 | 1/2021 | Ajithkumar et al. |
| 2021/0068446 A1 | 3/2021 | Keller et al. |
| 2021/0068447 A1 | 3/2021 | Keller et al. |
| 2021/0106516 A1 | 4/2021 | Nielsen |
| 2021/0106521 A1 | 4/2021 | Boesen et al. |
| 2021/0106534 A1 | 4/2021 | Wittorff |
| 2021/0112848 A1 | 4/2021 | Mua et al. |
| 2021/0161196 A1 | 6/2021 | Holton, Jr. |
| 2021/0169122 A1 | 6/2021 | St. Charles |
| 2021/0169125 A1 | 6/2021 | Holton, Jr. et al. |
| 2021/0169126 A1 | 6/2021 | Keller et al. |
| 2021/0169127 A1 | 6/2021 | Gao et al. |
| 2021/0169137 A1 | 6/2021 | McClanahan et al. |
| 2021/0169784 A1 | 6/2021 | Holton, Jr. et al. |
| 2021/0169786 A1 | 6/2021 | Holton, Jr. et al. |
| 2021/0169787 A1 | 6/2021 | Holton, Jr. et al. |
| 2021/0169791 A1 | 6/2021 | Johnson et al. |
| 2021/0169792 A1 | 6/2021 | Holton, Jr. et al. |
| 2021/0169806 A1 | 6/2021 | Hutchens et al. |
| 2021/0169808 A1 | 6/2021 | Wittorff |
| 2021/0169889 A1 | 6/2021 | Keller et al. |
| 2021/0170028 A1 | 6/2021 | Gerardi et al. |
| 2021/0170031 A1 | 6/2021 | Gerardi et al. |
| 2021/0177043 A1 | 6/2021 | Gerardi et al. |
| 2021/0177738 A1 | 6/2021 | Keller et al. |
| 2021/0195936 A1 | 7/2021 | Marshall et al. |
| 2021/0206554 A1 | 7/2021 | Holton, Jr. et al. |
| 2021/0251277 A1 | 8/2021 | McDermott et al. |
| 2021/0251977 A1 | 8/2021 | McCarty |
| 2021/0274830 A1 | 9/2021 | Strickland et al. |
| 2021/0290530 A1 | 9/2021 | Wittorff |
| 2021/0290547 A1 | 9/2021 | Wittorff |
| 2021/0299052 A1 | 9/2021 | Wittorff |
| 2021/0307375 A1 | 10/2021 | Stahl et al. |
| 2021/0329962 A1 | 10/2021 | Stahl et al. |
| 2021/0330590 A1 | 10/2021 | Hutchens et al. |
| 2021/0345656 A1 | 11/2021 | Nielsen et al. |
| 2021/0345657 A1 | 11/2021 | Gao et al. |
| 2021/0378258 A1 | 12/2021 | Cantrell et al. |
| 2021/0378948 A1 | 12/2021 | Gerardi et al. |
| 2021/0386662 A1 | 12/2021 | Axelsson et al. |

FOREIGN PATENT DOCUMENTS

| | | | |
|---|---|---|---|
| CA | 2303863 A1 * | 4/1999 |
| CN | 101569840 A | 11/2009 |
| CN | 102940307 A | 2/2013 |
| CN | 104997160 A | 10/2015 |
| CN | 106387990 B | 10/2018 |
| CN | 109998151 A | 7/2019 |
| CN | 110506984 A | 11/2019 |
| EP | 0627886 B1 | 1/2002 |
| EP | 0753998 B1 | 1/2003 |
| EP | 1334716 A1 | 8/2003 |
| EP | 0745380 B1 | 8/2005 |
| EP | 1578422 B1 | 4/2007 |

(56) References Cited

FOREIGN PATENT DOCUMENTS

| | | |
|---|---|---|
| EP | 1458388 B1 | 4/2009 |
| EP | 1383484 B1 | 4/2010 |
| EP | 2233134 A1 | 9/2010 |
| EP | 2269588 A1 | 1/2011 |
| EP | 2316418 A2 | 5/2011 |
| EP | 2343045 A2 | 7/2011 |
| EP | 2101598 B1 | 9/2011 |
| EP | 1894476 B1 | 5/2012 |
| EP | 1599186 B1 | 4/2013 |
| EP | 1926401 B1 | 1/2014 |
| EP | 2758040 A1 | 7/2014 |
| EP | 2152313 B1 | 9/2014 |
| EP | 2293786 B1 | 11/2014 |
| EP | 1998748 B1 | 1/2015 |
| EP | 2186507 B1 | 4/2015 |
| EP | 2555641 B1 | 5/2015 |
| EP | 2184057 B1 | 1/2016 |
| EP | 2790535 B1 | 2/2016 |
| EP | 2603101 B1 | 4/2016 |
| EP | 2691096 B1 | 7/2016 |
| EP | 2285411 B1 | 9/2016 |
| EP | 2838372 B1 | 6/2017 |
| EP | 2757909 B1 | 3/2018 |
| EP | 2811849 B1 | 4/2018 |
| EP | 1803443 B1 | 10/2018 |
| EP | 1803444 B1 | 10/2018 |
| EP | 3232825 B1 | 10/2018 |
| EP | 3065578 B1 | 12/2018 |
| EP | 1617823 B1 | 1/2019 |
| EP | 3473251 A1 | 4/2019 |
| EP | 3021691 B1 | 9/2019 |
| EP | 3603423 A1 | 2/2020 |
| EP | 3622834 A1 | 3/2020 |
| EP | 3104718 B9 | 4/2020 |
| EP | 2812000 B1 | 5/2020 |
| EP | 2768479 B1 | 7/2020 |
| EP | 3735972 A1 | 11/2020 |
| EP | 3744313 A1 | 12/2020 |
| EP | 2793600 B1 | 1/2021 |
| EP | 3541359 B1 | 1/2021 |
| EP | 3782474 A1 | 2/2021 |
| EP | 3541357 B1 | 4/2021 |
| EP | 3854383 A1 | 7/2021 |
| EP | 3868222 A1 | 8/2021 |
| EP | 3874970 A1 | 9/2021 |
| EP | 3773496 B1 | 12/2021 |
| FR | 2792200 B3 | 6/2001 |
| GB | 2469792 A | 11/2010 |
| JP | 5981123 B2 | 8/2016 |
| KR | 100381622 B1 | 4/2003 |
| NO | 20170683 A1 * | 10/2018 |
| WO | WO-93/00828 A2 | 1/1993 |
| WO | WO-02076211 A1 | 10/2002 |
| WO | WO-2006023399 A2 | 3/2006 |
| WO | WO-07/41035 A2 | 4/2007 |
| WO | WO-2008011169 A2 | 1/2008 |
| WO | WO-2009037319 A2 | 3/2009 |
| WO | WO-2010/031536 A1 | 3/2010 |
| WO | WO-2012125397 A2 | 9/2012 |
| WO | WO-2012/134380 A1 | 10/2012 |
| WO | WO-2013043866 A1 | 3/2013 |
| WO | WO-2014166845 A1 * | 10/2014 ............ A24B 13/00 |
| WO | WO-2015057603 A1 | 4/2015 |
| WO | WO-2015/090337 A1 | 6/2015 |
| WO | WO-2018009500 A1 | 1/2018 |
| WO | WO-2018093501 A1 | 5/2018 |
| WO | WO-2018197454 A1 | 11/2018 |
| WO | WO-2019/110074 A1 | 6/2019 |
| WO | WO-2019110073 A1 | 6/2019 |
| WO | WO-2019110075 A1 | 6/2019 |
| WO | WO-2019110076 A1 | 6/2019 |
| WO | WO-2019115778 A1 * | 6/2019 ............ A24B 13/00 |
| WO | WO-2019/207606 A1 | 10/2019 |
| WO | WO-2019219143 A1 | 11/2019 |
| WO | WO-2019219144 A1 | 11/2019 |
| WO | WO-2019219145 A1 | 11/2019 |
| WO | WO-2019219146 A1 | 11/2019 |
| WO | WO-2019219148 A1 | 11/2019 |
| WO | WO-2019219149 A1 | 11/2019 |
| WO | WO-2020157280 A1 | 8/2020 |
| WO | WO-2020239907 A1 | 12/2020 |
| WO | WO-2020244721 A1 | 12/2020 |
| WO | WO-2020244722 A1 | 12/2020 |
| WO | WO-2020244724 A1 | 12/2020 |
| WO | WO-2020244725 A1 | 12/2020 |
| WO | WO-2021004928 A1 | 1/2021 |
| WO | WO-2021021441 A1 | 2/2021 |
| WO | WO-2021053078 A1 | 3/2021 |
| WO | WO-2021069036 A1 | 4/2021 |
| WO | WO-2021/099571 A1 | 5/2021 |
| WO | WO-2021086367 A1 | 5/2021 |
| WO | WO-2021/116834 A1 | 6/2021 |
| WO | WO-2021116823 A1 | 6/2021 |
| WO | WO-2021116825 A1 | 6/2021 |
| WO | WO-2021116852 A1 | 6/2021 |
| WO | WO-2021116855 A1 | 6/2021 |
| WO | WO-2021116865 A1 | 6/2021 |
| WO | WO-2021144365 A1 | 7/2021 |
| WO | WO-2021144367 A1 | 7/2021 |
| WO | WO-2021219624 A1 | 11/2021 |
| WO | WO-2021244714 A1 | 12/2021 |

OTHER PUBLICATIONS

Dupont, Avicel PH 302, Product overview and specifications, copyright 2018 (Year: 2018).*
International Search Report and Written Opinion dated Mar. 1, 2022, issued in corresponding International Patent Application No. PCT/US2021/060643.
International Search Report and Written Opinion dated Mar. 3, 2022, issued in corresponding International Patent Application No. PCT/US2021/060697.
International Search Report and Written Opinion dated Mar. 16, 2022, issued in corresponding International Patent Application No. PCT/US2021/060497.
Stuart L. Cantor et al., "Chapter 8: Pharmaceutical Granulation Processes, Mechanism, and the Use of Binders" *Pharmaceutical Dosage Forms: Tablets—Unit Operations and Mechanical Properties*, Jun. 2008.
Camilla Sander et al., Process development for spray drying of sticky pharmaceuticals; case study of bioadhesive nicotine microparticles for compressed medicated chewing gum *International Journal of Pharmaceutics*, vol. 452, Issues 1-2, Aug. 2013, pp. 434-437.
International Search Report and Written Opinion dated Mar. 25, 2022, issued in corresponding International Patent Application No. PCT/US2021/060782.
Examination report from the European Union Patent Office dated Oct. 14, 2021, for corresponding European Community design registration Nos. 008716138-0001-008716138-0018.
International Search Report and Written Opinion dated Mar. 4, 2022, issued in corresponding International Patent Application No. PCT/US2021/060638.
International Search Report and Written Opinion dated Mar. 25, 2022, issued in corresponding International Patent Application No. PCT/US2021/060785.
International Search Report and Written Opinion dated Mar. 4, 2022, issued in corresponding International Patent Application No. PCT/US2021/060640.
International Search Report and Written Opinion dated Mar. 22, 2022, issued in corresponding International Patent Application No. PCT/US2021/060796.
Office Action dated Sep. 23, 2022, issued in corresponding U.S. Appl. No. 17/223,746.
Office Action dated Oct. 5, 2022, issued in corresponding U.S. Appl. No. 17/223,756.
Office Action dated Dec. 8, 2022, issued in corresponding U.S. Appl. No. 17/223,800.
Office Action dated Jan. 31, 2023, issued in corresponding U.S. Appl. No. 17/223,415.

(56) References Cited

OTHER PUBLICATIONS

International Search Report and Written Opinion dated May 8, 2023, issued in corresponding International Application No. PCT/US2023/060290.
Office Action dated Feb. 23, 2023, issued in corresponding U.S. Appl. No. 17/223,709.
Office Action dated Mar. 30, 2023, issued in corresponding U.S. Appl. No. 17/223,756.
Office Action dated Apr. 7, 2023, issued in corresponding U.S. Appl. No. 17/223,746.
Mayo Clinic (https://www.mayoclinic.org/healthy-lifestyle/nutrition-and-healthy-eating/in-depth/caffeine/art-20045678, retrieved Aug. 20, 2024).
Office Action for corresponding U.S. Appl. No. 18/533,778 dated Aug. 30, 2024 (29 pages).

* cited by examiner

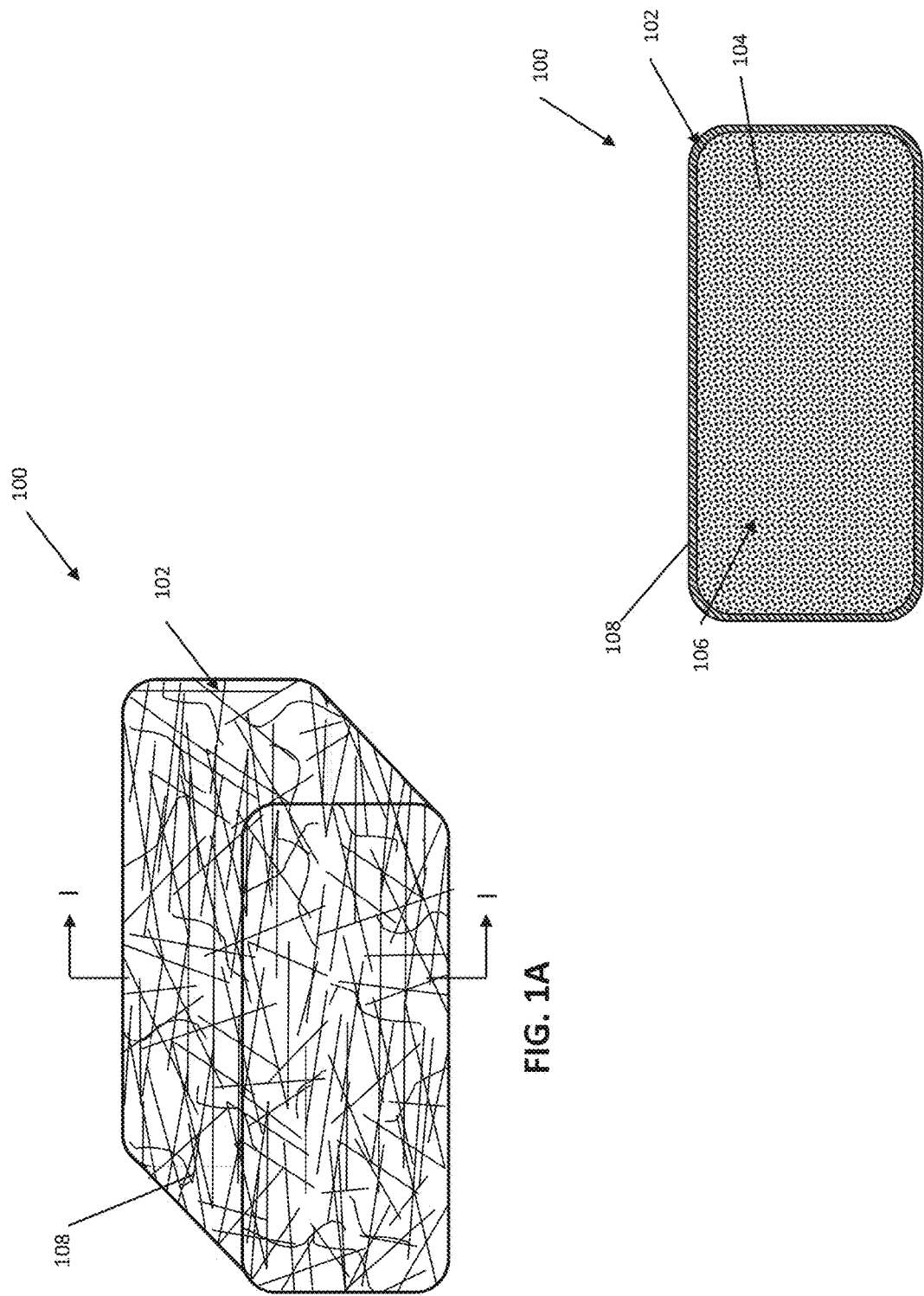

| Sample | Oil Phase | Aqueous Phase | Oil-to-Aqueous Phase Ratio (v/v) | Target Nicotine Concentration (mg/g) | Oil Density (g/mL) | Target Nicotine Concentration (mg/mL) | Concentration of Nicotine in Aqueous Phase (mg/mL) | Concentration of Nicotine in Oil Phase (mg/mL) | Partition Coefficient |
|---|---|---|---|---|---|---|---|---|---|
| 1 | Medium-Chain Triglyceride (MCT) Oil | DI Water | 50-50 | 200 | 0.938 | 187.6 | 89.12 | 98.48 | 1.105 |
| 2 | MCT Oil | Basified DI Water (pH = 7.4) | 50-50 | 200 | 0.938 | 187.6 | 90.22 | 97.38 | 1.079 |
| 3 | MCT Oil | Artificial Saliva (pH = 6.8) | 50-50 | 200 | 0.938 | 187.6 | 90.02 | 97.58 | 1.084 |
| 4 | MCT Oil | Acidified DI Water (pH = 2) | 50-50 | 200 | 0.938 | 187.6 | 87.983 | 99.617 | 1.132 |
| 5 | MCT Oil | Acidic Buffer, 1M (pH = 2) | 50-50 | 200 | 0.938 | 187.6 | 137.66 | 49.94 | 0.363 |
| 6 | MCT Oil | Acidic Buffer, 1M (pH = 2) | 50-50 | 0.5 | 0.938 | 0.469 | 0.392 | 0.077 | 0.197 |
| 7 | Triacetin Oil | Acidic Buffer, 1M (pH = 2) | 50-50 | 0.5 | 1.16 | 0.58 | 0.58 | 0 | 0 |
| 8 | Triolein Oil | Acidic Buffer, 1M (pH = 2) | 50-50 | 0.5 | 0.915 | 0.458 | 0.272 | 0.186 | 0.684 |

FIG. 6A

ORAL POUCH PRODUCT

BACKGROUND

Field

The present disclosure relates to oral pouch products including nicotine.

Description of Related Art

Oral nicotine products are available in a variety of formats, such as gums, sprays, lozenges, dissolvable tablets, non-dissolvable chews, films, gels, capsules, sticks (e.g., coated wooden dowels or singular dissolvable sticks), and pouches (e.g., containing fibers or granules). Oral products may have nicotine levels that create a familiar experience for adult tobacco consumers.

SUMMARY

At least one example embodiment relates to an oral pouch product.

In at least one example embodiment, the oral pouch product includes a wrapper and a filling material. The wrapper defines a cavity. The filling material is in the cavity. The filling material includes a dry mixture and a liquid mixture. The dry mixture includes a cellulosic material and a water-soluble filler. The liquid mixture includes an oil and liquid nicotine. The oil includes a triglyceride, a diglyceride, a monoglyceride, or any combination thereof. The liquid nicotine is dissolved in the oil. The filling material is free of water or includes water in an amount less than or equal to 5 weight percent.

In at least one example embodiment, the filling material is free of glycerin and propylene glycol.

In at least one example embodiment, the cellulosic material includes microcrystalline cellulose (MCC).

In at least one example embodiment, the MCC includes particles having a size ranging from 100 microns to 300 microns.

In at least one example embodiment, the MCC is wood pulp-derived MCC.

In at least one example embodiment, the filling material includes the cellulosic material in an amount ranging from 10 weight percent to 70 weight percent.

In at least one example embodiment, the filling material includes the cellulosic material in an amount ranging from 30 weight percent to 60 weight percent.

In at least one example embodiment, the filling material includes the oil in an amount ranging from 10 weight percent to 50 weight percent.

In at least one example embodiment, the filling material includes the oil in an amount ranging from 15 weight percent to 25 weight percent.

In at least one example embodiment, the oil consists essentially of a triglyceride, a diglyceride, a monoglyceride, or any combination thereof.

In at least one example embodiment, the oil includes the triglyceride.

In at least one example embodiment, the triglyceride includes a medium chain triglyceride.

In at least one example embodiment, the filling material includes the water-soluble filler in an amount ranging from 10 weight percent to 50 weight percent.

In at least one example embodiment, the water-soluble filler includes a sugar alcohol, a sugar, a maltodextrin, a starch, a polysaccharide, or any combination thereof.

In at least one example embodiment, the water-soluble filler includes the sugar alcohol.

In at least one example embodiment, the filling material includes the sugar alcohol in an amount ranging from 15 weight percent to 25 weight percent.

In at least one example embodiment, the sugar alcohol includes xylitol.

In at least one example embodiment, the filling material further comprises a pH adjuster.

In at least one example embodiment, the pH adjuster includes sodium bicarbonate.

In at least one example embodiment, the filling material further includes an antioxidant.

In at least one example embodiment, the antioxidant includes Tocopherol, or a tocopherol derivative, ascorbic acid, an ascorbic acid derivative, tert-butylhydroquinone, or any combination thereof.

In at least one example embodiment, the filling material includes the antioxidant in an amount less than 2 weight percent.

In at least one example embodiment, the filling material further includes an flavorant.

In at least one example embodiment, wherein the filling material includes the flavorant in an amount less than 10 weight percent.

In at least one example embodiment, the filling material includes the flavorant in an amount ranging from 0.1 weight percent to 5 weight percent.

In at least one example embodiment, the filling material includes the liquid nicotine in an amount ranging from 0.1 weight percent to 10 weight percent.

In at least one example embodiment, the liquid nicotine includes tobacco-derived nicotine.

In at least one example embodiment, the liquid nicotine includes synthetic nicotine.

In at least one example embodiment, the wrapper includes an elastomer.

In at least one example embodiment, the elastomer is white.

In at least one example embodiment, the elastomer includes polyurethane.

In at least one example embodiment, the wrapper has a basis weight ranging from 20 grams per meter (gsm) to 30 gsm.

At least one example embodiment relates to an oral pouch product.

In at least one example embodiment, the oral pouch product includes a wrapper and a filling material. The wrapper defines a cavity. The wrapper includes an elastomer. The filling material is in the cavity. The filling material includes a dry mixture and a liquid mixture. The dry mixture includes a cellulosic material and a water-soluble filler. The liquid mixture includes an oil and liquid nicotine. The oil includes a triglyceride, a diglyceride, a monoglyceride, or any combination thereof.

At least one example embodiment, relates to an oral pouch product.

In at least one example embodiment, the oral pouch product includes a wrapper and a filling material. The wrapper defines a cavity. The filling material is in the cavity. The filling material includes a dry mixture and a liquid mixture. The dry mixture includes microcrystalline cellulose and a water-soluble filler. The microcrystalline cellulose is present in an amount ranging from 10 weight percent to 70 weight percent. The water-soluble filler is present in an amount ranging from 10 weight percent to 50 weight percent. The water-soluble filler includes a sugar alcohol. The liquid mixture includes a triglyceride. The triglyceride is present in an amount ranging from 10 weight percent to 30 weight percent. The liquid nicotine is dissolved in the triglyceride. The filling material is free of glycerin and propylene glycol. The filling material is either free of water or includes water in an amount less than 5 weight percent of the filling material.

In at least one example embodiment, the wrapper includes an elastomer.

In at least one example embodiment, the elastomer includes polyurethane.

At least one example embodiment relates to a method of making an oral pouch product.

In at least one example embodiment, the method comprises preparing a liquid mixture including liquid nicotine and an oil. The oil includes a triglyceride, a diglyceride, a monoglyceride, or any combination thereof. At least a portion of the nicotine is dissolved in the oil. The method further comprises preparing a dry mixture including a cellulosic material and a water-soluble filler. The method further includes forming a filling material by admixing the liquid mixture and the dry mixture. The method further includes forming oral pouch product by enclosing the filling material in cavity defined by a wrapper.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 1A is a perspective view of an oral pouch product according to at least one example embodiment.

FIG. 1B is a cross-sectional view of the oral pouch product taken along line I-I of FIG. 1A according to at least one example embodiment.

FIG. 6A is a table depicting partition coefficient data for nicotine in different oil and aqueous phases.

DETAILED DESCRIPTION OF EXAMPLE EMBODIMENTS

Figure 2A:
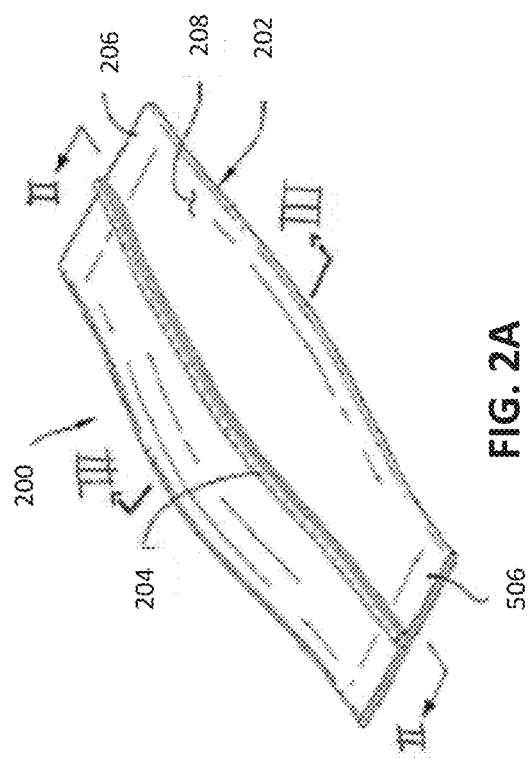
FIG. 2A is a perspective view of an oral pouch product according to at least one example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc., may be used herein to describe various elements, regions, layers and/or sections, these elements, regions, layers, and/or sections should not be limited by these terms. These terms are only used to distinguish one element, region, layer, or section from another region, layer, or section. Thus, a first element, component, region, layer, or section discussed below could be termed a second element, region, layer, or section without departing from the teachings of example embodiments.

Spatially relative terms (e.g., "beneath," "below," "lower," "above," "upper," "inside," "outside," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," specify the presence of stated features, integers, steps, operations, and/or elements, but do not preclude the presence or addition of one or more other features, integers, steps, operations, elements, and/or groups thereof.

Example embodiments are described herein with reference to cross-sectional illustrations that are schematic illustrations of example embodiments. As such, variations from the shapes of the illustrations are to be expected. Thus, example embodiments should not be construed as limited to the shapes of regions illustrated herein but are to include deviations and variations in shapes. When the terms "about" or "substantially" are used in connection with a numerical value, it is intended that the associated numerical value include a tolerance of ±10% around the stated numerical value unless the context indicates otherwise.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

In at least one example embodiment, methods of enhancing flavor and/or sensory effects of nicotine in oral products, such as oral pouch products including nicotine and cellulose in a pouch wrapper are provided.

In at least one example embodiment, the oral pouch product includes a tobacco extract, such as a tobacco-derived nicotine extract, and/or synthetic nicotine. The oral pouch product may include nicotine alone or in combination with a carrier (e.g., white snus), such as a cellulosic material. The carrier may be a non-tobacco material (e.g., microcrystalline cellulose). In some example embodiments, the carrier may also include a tobacco material (e.g., tobacco fibers having reduced or eliminated nicotine content, which may be referred to as "exhausted tobacco plant tissue or fibers"). In some example embodiments, the exhausted tobacco plant tissue or fibers can be treated to remove at least 25%, 40%, 50%, 60%, 70%, 75%, 80%, 85%, 90%, or 95% of the nicotine. For example, the tobacco plant tissue can be washed with water or another solvent to remove the nicotine.

In other example embodiments, the oral pouch product may include *cannabis*, such as *cannabis* plant tissue and/or *cannabis* extracts. In at least one example embodiment, the *cannabis* material includes leaf and/or flower material from one or more species of *cannabis* plants and/or extracts from the one or more species of *cannabis* plants. The one or more species of *cannabis* plants may include *Cannabis sativa*, *Cannabis indica*, and/or *Cannabis ruderalis*. In at least one example embodiment, the *cannabis* may be in the form of fibers. In at least one example embodiment, the *cannabis* may include a cannabinoid, a terpene, and/or a flavonoid. In at least one example embodiment, the *cannabis* material may be a *cannabis*-derived *cannabis* material, such as a *cannabis*-derived cannabinoid, a *cannabis*-derived terpene, and/or a *cannabis*-derived flavonoid.

The oral pouch product may have various ranges of oven volatiles. In at least one example embodiment, the oral pouch product is a dry oral pouch product having a moisture content of less than 10 weight percent (e.g., 0.5 weight percent to 10 weight percent, or about 2 weight percent to about 4 weight percent). In at least one example embodiment, the oral pouch product has a medium moisture content, such as a moisture content ranging from 20 weight percent to 35 weight percent. In at least one example embodiment, the oral pouch product is a wet oral pouch product having a moisture content ranging from 40 weight percent to 55 weight percent.

In at least one example embodiment, oral pouch product may further include one or more elements such as a mouth-stable polymer, a mouth-soluble polymer, a sweetener (e.g., a synthetic sweetener and/or a natural sweetener), an energizing agent, a soothing agent, a focusing agent, a plasticizer, mouth-soluble fibers, an alkaloid, a mineral, a vitamin, a dietary supplement, a nutraceutical, a coloring agent (natural and/or artificial), an amino acid, a chemesthetic agent, an antioxidant, a food-grade emulsifier and/or surfactant, a pH modifier, a botanical, a tooth-whitening agent, a therapeutic agent, a processing aid, a stearate, a wax, a stabilizer, a disintegrating agent, a lubricant, a preservative, a filler, a flavorant, flavor masking agents, a bitterness receptor site blocker, a receptor site enhancers, other additives, or any combination thereof.

Oral Pouch Product

FIG. 1A is a perspective view of an oral pouch product according to at least one example embodiment.

FIG. 1B is a cross sectional view of the oral pouch product taken at line I-I of FIG. 1A according to at least one example embodiment.

In at least one example embodiment, as shown in FIGS. 1A-1B, an oral pouch product 100 is configured to fit in an adult consumer's mouth. The oral pouch product 100 includes a pouch wrapper 102 and an inner filling material 104. The filling material 104 is in an inner cavity 106 at least partially defined by the pouch wrapper 102. For example, an adult consumer can suck, chew, or otherwise orally manipulate the oral pouch product 100 to release flavor and/or functional ingredients contained therein.

The filling material 104 includes a dry mixture and a liquid mixture, such as the liquid mixture described herein with respect to FIGS. 4A-6D. At least a portion of the liquid mixture is absorbed on the dry mixture. In at least one example embodiment, all of the liquid mixture is absorbed on the dry mixture. The liquid mixture includes an oil and an active pharmaceutical ingredient (API), such as nicotine. The dry mixture includes an insoluble material or carrier, such as a cellulosic material.

In at least one example embodiment, the API includes nicotine and the oral pouch product 100 includes the oil and the nicotine in the amounts and ratios described above with respect to FIGS. 4A-6D. In at least one example embodiment, the API includes one or more tobacco extracts, nicotine, one or more *cannabis* extracts, and/or one or more cannabinoids. The nicotine may include tobacco-derived nicotine and/or synthetic nicotine. In at least one example embodiment, the API includes liquid nicotine. The cannabinoid may include tetrahydrocannabinol ("THC") and/or cannabidiol ("CBD").

The oral pouch product 100 may include the API in an amount greater than or equal to about 0.1 weight percent (e.g., greater than or equal to about 0.5 weight percent, greater than or equal to about 1 weight percent, greater than or equal to about 2 weight percent, greater than or equal to about 3 weight percent, greater than or equal to about 4 weight percent, greater than or equal to about 5 weight percent, greater than or equal to about 6 weight percent, greater than or equal to about 7 weight percent, greater than or equal to about 8 weight percent, or greater than or equal to about 9 weight percent). The oral pouch product 100 may include the API in an amount less than or equal to about 10 weight percent (e.g., less than or equal to about 9 weight percent, less than or equal to about 8 weight percent, less than or equal to about 7 weight percent, less than or equal to about 6 weight percent, less than or equal to about 5 weight percent, less than or equal to about 4 weight percent, less than or equal to about 3 weight percent, less than or equal to about 2 weight percent, less than or equal to about 1 weight percent, or less than or equal to about 0.5 weight percent).

In at least one example embodiment, the oil of the liquid mixture includes one or more triglycerides, one or more diglycerides, one or more monoglycerides, triacetin, triolein, trilinolein, vegetable oil, one or more partially-hydrogenated oils, or any combination thereof. In at least one example embodiment, the oil consists essentially of one or more triglycerides, one or more diglycerides, one or more monoglycerides, or any combination thereof. In at least one example embodiment, the oil consists essentially of the triglyceride. The triglyceride may include LCT, MCT, SCT, or any combination thereof. In at least one example embodiment, the triglyceride consists essentially of MCT. In at least one example embodiment, the filling material 104 includes the oil in an amount greater than or equal to about 0.5 weight percent (e.g., greater than or equal to about 1 weight percent, greater than or equal to about 5 weight percent, greater than or equal to about 10 weight percent, greater than or equal to about 15 weight percent, greater than or equal to about 20 weight percent, greater than or equal to about 25 weight percent, greater than or equal to about 30 weight percent, greater than or equal to about 35 weight percent, greater than or equal to about 40 weight percent, or greater than or equal to about 45 weight percent). The filling material 104 may include the oil in an amount less than or equal to about 50 weight percent (e.g., less than or equal to about 45 weight percent, less than or equal to about 40 weight percent, less than or equal to about 35 weight percent, less than or equal to about 30 weight percent, less than or equal to about 25 weight percent, less than or equal to about 20 weight percent, less than or equal to about 15 weight percent, less than or equal to about 10 weight percent, less than or equal to about 5 weight percent, or less than or equal to about 1 weight percent). In at least one example embodiment, the oral pouch product 100 includes the oil in an amount ranging from 10 weight percent to 50 weight percent (e.g., about 10 weight percent to about 25 weight percent, or about 15 weight percent to about 25 weight percent).

In at least one example embodiment, the filling material 104 includes water in amount less than or equal to about 5 weight percent (e.g., less than or equal to about 4 weight percent, less than or equal to about 3 weight percent, less than or equal to about 2 weight percent, less than or equal to about 1 weight percent, less than or equal to about 0.5 weight percent, or less than or equal to about 0.25 weight percent). In at least one example embodiment, no water is intentionally added to the liquid mixture. However, a small amount of water may come into contact with the liquid mixture via other elements in the oral pouch product. In at least one example embodiment, the low water content may slow down nicotine degradation and oxidation compared to oral pouch products having higher water content. In at least one example embodiment, the filling material 104 is free of water.

By including a higher level of oil, such as MCT, the oral pouch product 100 maintains a relatively moist mouth feel, while maintaining low water content and a water activity level below about 0.7, which can aid in preventing and/or reducing microbial growth and increasing stability of nicotine in the oral pouch product 100. Further, when the wrapper 102 is hydrophobic, since the inner filling material predominately includes oils instead of water, the flavors from the filling material 104 more readily pass through the pouch wrapper 102 than where a hydrophilic pouch wrapper is used.

In at least one example embodiment, a weight ratio of the dry mixture to the liquid mixture may be greater than or equal to about 60:40 (e.g., greater than or equal to about 65:35, greater than or equal to about 70:30, greater than or equal to about 75:25, greater than or equal to about 80:20, greater than or equal to about 85:15, greater than or equal to about 90:10, or greater than or equal to about 95:5).

In at least one example embodiment, the dry mixture includes an insoluble material. At least a portion of the liquid mixture may be absorbed in the insoluble material, as described below with respect to FIGS. 1A-3D. In at least one example embodiment, all of the liquid mixture is absorbed in the insoluble material.

In at least one example embodiment, the insoluble material is a cellulosic material. The cellulosic material may include or be derived from sugar beets, wood pulp, cotton, bran, citrus pulp, grass (e.g., switch grass), willow, poplar, or any combination thereof. The insoluble cellulosic material may be a treated cellulosic material, such as microcrystalline cellulose ("MCC"), carboxymethyl cellulose ("CMC"), hydroxypropyl methylcellulose ("HPMC"), hydroxypropyl cellulose ("HPC"), or any combination thereof. In at least one example embodiment, the cellulosic material includes mouth-insoluble cellulosic fibers. In at least one example embodiment, the cellulosic material includes MCC. In at least one example embodiment, the MCC includes wood pulp-derived MCC.

In at least one example embodiment, the insoluble material includes water-insoluble fibers. The water-insoluble fibers may include water-insoluble polymeric fibers. The water-insoluble polymer fibers may include polypropylene, polyester, polyethylene, polyurethane, or any combination thereof.

In at least one example embodiment, the filling material 104 includes the insoluble material in an amount greater than or equal to about 10 weight percent (e.g., greater than or equal to about 15 weight percent, greater than or equal to about 20 weight percent, greater than or equal to about 25 weight percent, greater than or equal to about 30 weight percent, greater than or equal to about 35 weight percent, greater than or equal to about 40 weight percent, greater than or equal to about 45 weight percent, greater than or equal to about 50 weight percent, greater than or equal to about 55 weight percent, greater than or equal to about 60 weight percent, greater than or equal to about 65 weight percent, greater than or equal to about 70 weight percent, or greater than or equal to about 75 weight percent). The filling material 104 may include the insoluble material in an amount less than or equal to about 80 weight percent (e.g., less than or equal to about 75 weight percent, less than or equal to about 70 weight percent, less than or equal to about 65 weight percent, less than or equal to about 60 weight percent, less than or equal to about 55 weight percent, less than or equal to about 50 weight percent, less than or equal to about 45 weight percent, less than or equal to about 40 weight percent, less than or equal to about 35 weight percent, less than or equal to about 30 weight percent, less than or equal to about 25 weight percent, less than or equal to about 20 weight percent, or less than or equal to about 15 weight percent). In at least one example embodiment, the filling material 104 includes the insoluble material in an amount ranging from 10 weight percent to 70 weight percent (e.g., about 30 weight percent to about 60 weight percent).

In at least one example embodiment, the insoluble material has a particle size of greater than or equal to about 50 microns (e.g., greater than or equal to about 100 microns, greater than or equal to about 150 microns, greater than or equal to about 200 microns, greater than or equal to about 250 microns, greater than or equal to about 300 microns, greater than or equal to about 350 microns, greater than or equal to about 400 microns, or greater than or equal to about 450 microns). The particle size may be less than or equal to about 500 microns (e.g., less than or equal to about 450 microns, less than or equal to about 400 microns, less than or equal to about 350 microns, less than or equal to about 300 microns, less than or equal to about 250 microns, less than or equal to about 200 microns, less than or equal to about 150 microns, or less than or equal to about 100 microns).

In at least one example embodiment, the dry mixture further includes a water-soluble filler. The water-soluble filler may include one or more sweeteners, maltodextrin, psyllium, starch, one or more polysaccharides, one or more salts, one or more synthetic polymers, dietary fibers, or any combination thereof. The filling material 104 may include the water-soluble filler in an amount greater than or equal to about 10 weight percent (e.g., greater than or equal to about 15 weight percent, greater than or equal to about 20 weight percent, greater than or equal to about 25 weight percent, greater than or equal to about 30 weight percent, greater than or equal to about 35 weight percent, greater than or equal to about 40 weight percent, or greater than or equal to about 45 weight percent). The filling material 104 may include the water-soluble filler in an amount less than or equal to about 50 weight percent (e.g., less than or equal to about 45 weight percent, less than or equal to about 40 weight percent, less than or equal to about 35 weight percent, less than or equal to about 30 weight percent, less than or equal to about 25 weight percent, less than or equal to about 20 weight percent, or less than or equal to about 15 weight percent).

In at least one example embodiment, the filling material 104 includes at least one sweetener. The sweetener may include a synthetic sweetener and/or a natural sweetener. The natural sweetener may include one or more sugars, such as a monosaccharide, a disaccharide, and/or a polysaccharide (e.g., xylose, ribose, mannose). In at least one example embodiment, the sweetener includes a natural sweetener including sucrose (i.e., table sugar), honey, low-molecular-weight sugars excluding sucrose, glucose (i.e., grape sugar, corn sugar, dextrose), molasses, corn sweetener, glucose syrup (i.e., corn syrup), fructose (i.e., fruit sugar), lactose (i.e., milk sugar), maltose (i.e., malt sugar, maltobiose), sorghum syrup, fruit juice concentrate, or any combination thereof. In at least one example embodiment, the sweetener includes a non-nutritive sweetener including stevia, saccharin, aspartame, sucralose, acesulfame potassium, or any combination thereof. The sweetener may include a high-intensity sweetener. The high-intensity sweetener may be sucralose, palatinose, stevia, Acesulfame K, glycyrrhizic acid, or any combination thereof.

In at one example embodiment, the sweetener includes one or more sugar alcohols. The sugar alcohols may include ethylene glycol, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, or any combination thereof. The filling material 404 may include the sugar alcohol in an amount greater than or equal to about 10 weight percent (e.g., greater than or equal to about 15 weight percent, greater than or equal to about 20 weight percent, greater than or equal to about 25 weight percent, greater than or equal to about 30 weight percent, greater than or equal to about 35 weight percent, greater than or equal to about 40 weight percent, or greater than or equal to about 45 weight percent). The filling material 104 may include the sugar alcohols in an amount less than or equal to about 50 weight percent (e.g., less than or equal to about 45 weight percent, less than or equal to about 40 weight percent, less than or equal to about 35 weight percent, less than or equal to about 30 weight percent, less than or equal to about 25 weight percent, less than or equal to about 20 weight percent, or less than or equal to about 15 weight percent). In at least one example embodiment, the filling material 104 includes the sugar alcohol in an amount ranging from about 15 weight percent to about 25 weight percent (e.g., about 18 weight percent to about 22 weight percent).

In at least one example embodiment, the filling material 104 includes a pH adjuster. The pH adjuster may be included in the dry mixture, such as a water-soluble filler. The pH adjuster may include ammonium carbonate, ammonium bicarbonate, ammonium hydroxide, calcium carbonate, potassium carbonate, potassium bicarbonate, potassium hydroxide, sodium carbonate, sodium bicarbonate, sodium hydroxide, or any combination thereof. The pH adjuster may be included in an amount greater than or equal to about 0.01 weight percent (e.g., greater than or equal to about 0.05 weight percent, greater than or equal to about 0.1 weight percent, greater than or equal to about 0.5 weight percent, greater than or equal to about 1 weight percent, greater than or equal to about 2 weight percent, greater than or equal to about 3 weight percent, greater than or equal to about 4 weight percent, greater than or equal to about 5 weight percent, greater than or equal to about 6 weight percent, greater than or equal to about 7 weight percent, greater than or equal to about 8 weight percent, or greater than or equal to about 9 weight percent). The pH adjuster may be included in an amount less than or equal to about 2 weight percent (e.g., less than or equal to about 10 weight percent, less than or equal to about 9 weight percent, less than or equal to about 8 weight percent, less than or equal to about 7 weight percent, less than or equal to about 6 weight percent, less than or equal to about 5 weight percent, less than or equal to about 4 weight percent, less than or equal to about 3 weight percent, less than or equal to about 2 weight percent, less than or equal to about 1 weight percent, less than or equal to about 0.5 weight percent, less than or equal to about 0.1 weight percent, or less than or equal to about 0.05 weight percent). In at least one example embodiment, the pH adjuster is present in an amount ranging from about 4 weight percent to about 6 weight percent. In at least one other example embodiment, the pH adjuster is present in an amount ranging from about 0.01 weight percent to about 2 weight percent. In at least one other example embodiment, the oral pouch product is free of a pH adjuster.

In at least one example embodiment, the oral pouch product is free of humectants. In at least one example embodiment, the oral pouch product is free of glycerin and/or propylene glycol.

In at least one example embodiment, the filling material 104 includes an antioxidant. The antioxidant may be one or more oil-phase antioxidants, one or more water-phase antioxidants, one or more dry antioxidants, or any combination thereof. The antioxidant may include tocopherol, a tocopherol derivative, ascorbic acid, an ascorbic acid derivative (e.g., ascorbyl palmitate, sodium ascorbate), tert-butylhydroquinone (TBHQ), butylated hydroxytoluene (BHT), butylated hydroxyanisole (BHA), vitamin C, vitamin B, magnesium, calcium, or any combination thereof, by way of example. The filling material 104 may include the antioxidant in an amount less than or equal to about 5 weight percent (e.g., less than or equal to about 4 weight percent, less than or equal to about 3 weight percent, less than or equal to about 2 weight percent, less than or equal to about 1 weight percent, or less than or equal to about 0.5 weight percent).

In at least one example embodiment, the filling material 104 includes one or more flavorants. The flavorants may be provided in the liquid mixture, the dry mixture, or separately (e.g., water-based flavorants, as discussed below in conjunction with FIG. 7). The flavorant may include an oil-phase flavorant and/or a water/phase flavorant. The flavorant may be natural or artificial. In at least one example embodiment, the flavorant includes a fruit flavorant (e.g., bergamot, berry, cherry, lemon, and/or orange), a liquor or liqueur flavorant (e.g., bourbon, cognac, scotch, whiskey, and/or DRAMBUIE brand liqueur), a mint flavorant (e.g., Japanese mint, menthol, peppermint, spearmint, wintergreen, and/or mint oils from a species of the genus Mentha), a floral flavorant (e.g., geranium, lavender, and/or rose), a spice, an herb, or another botanical or botanical-derived flavorant (e.g., anise, apium graveolens, caraway, cardamom, cascarilla, cassia, cinnamon, chamomile, clove, cocoa, coffee, coriander, fennel, ginger, jasmine, licorice, nutmeg, pimenta, sage, sandalwood vanilla, and/or ylang-ylang), honey essence, or any combination thereof. In at least one example embodiment, the flavorant includes bergamot, berry, cherry, lemon, orange, bourbon, cognac, scotch, whiskey, DRAMBUIE brand liqueur, Japanese mint, menthol, peppermint, spearmint, wintergreen, mint oils from a species of the genus Mentha, geranium, lavender, rose, anise, apium graveolens, caraway, cardamom, cascarilla, cassia, cinnamon, chamomile, clove, coffee, coriander, fennel, ginger, jasmine, licorice, nutmeg, pimenta, sage, sandalwood vanilla, ylang-ylang, honey essence, or any combination thereof. In at least one example embodiment, the oral pouch product includes an encapsulated flavorant. In at least one example embodiment, the filling material 104 includes the flavorant in an amount greater than or equal to about 0.01 weight percent (e.g., greater than or equal to about 0.1 weight percent, greater than or equal to about 0.5 weight percent, greater than or equal to about 1 weight percent, greater than or equal to about 2 weight percent, greater than or equal to about 4 weight percent, greater than or equal to about 5 weight percent, greater than or equal to about 8 weight percent, greater than or equal to about 10 weight percent, greater than or equal to about 15 weight percent, or greater than or equal to about 20 weight percent). The filling material 104 may include the one or flavorants in an amount less than or equal to about 25 weight percent (e.g., less than or equal to about 20 weight percent, less than or equal to about 15 weight percent, less than or equal to about 10 weight percent, greater than or equal to about 8 weight percent, less than or equal to about 5 weight percent, less than or equal to about 4 weight percent, greater than or equal to about 2 weight percent, less than or equal to about 1 weight percent, or less than or equal to about 0.5 weight percent, less than or equal to about 0.1 weight percent). In at least one example embodiment, the filling material 104 includes the flavorant in an amount ranging from about 0.1 weight percent to about 10 weight percent (e.g., about 0.1 weight percent to about 4 weight percent).

In at least one example embodiment, the filling material 104 includes an emulsifier and/or surfactant. The emulsifier and/or surfactant may include lecithin, glycerol monosterate, a polysorbate, a poloxamer, or a combination of lecithin and glycerol monostearate. The emulsifier and/or surfactant may be present in an amount greater than 0 weight percent (e.g., greater than or equal to about 0.5 weight percent, greater than or equal to about 0.75 weight percent, greater than or equal to about 1 weight percent, greater than or equal to about 2 weight percent, greater than or equal to about 3 weight percent, or greater than or equal to about 4 weight percent). The emulsifier and/or surfactant may be present in an amount less than or equal to about 5 weight percent (e.g., less than or equal to about 4 weight percent, less than or equal to about 3 weight percent, less than or equal to about 2 weight percent, less than or equal to about 1 weight percent, less than or equal to about 0.75 weight percent, or less than or equal to about 0.5 weight percent). In at least one example embodiment, the emulsifier and/or surfactant is present in an amount ranging from 0.1 weight percent to about 2 weight percent.

In at least one example embodiment, the dry mixture may additionally or alternatively include *cannabis*. The *cannabis* can include any portion of the *cannabis* plant and/or any extract therefrom. For example, in some example embodiments, the plant material may include a mixture of *Cannabis sativa* and *Cannabis indica*, such as, for example only, a mixture of about 70% *sativa* and about 30% indica. In at least one example embodiment, the oral pouch product 100 may include a *cannabis* extract applied to an insoluble filler, such as cellulose. In at least one example embodiment, the oral pouch product 100 may include *cannabis* in addition to other plant material. Alternatively, the oral pouch product 100 may include other plant materials, such as herbs, vegetables, and the like.

In at least one example embodiment, prior to placement of the *cannabis* (or other plant material) in the oral pouch product 100, the *cannabis* (or other plant material) may be heated to a temperature sufficient to decarboxylate a compound within the *cannabis* (or other plant material). For example, *cannabis* may be maintained at the heated temperature for a time period that is sufficient to cause decarboxylation (i.e., to convert tetrahydrocannabinolic acid ("THCA") that is present in the *cannabis* to THC, and/or to convert cannabidiolic acid ("CBDA") to CBD). For some applications, maintaining the plant material at the heated temperature causes the decarboxylation of the *cannabis* in accordance with an article by Dussy, et al., entitled "Isolation of Delta9-THCA-A from hemp and analytical aspects concerning the determination of Delta9-THC in *cannabis* products (Forensic Sci. Int. 2005 Apr. 20; 149(1):3-10), the entire disclosure of which is incorporated herein by reference, and/or an article by Veress, et al., entitled "Determination of cannabinoid acids by high-performance liquid chromatography of their neutral derivatives formed by thermal decarboxylation: I. Study of the decarboxylation process in open reactors" (Journal of Chromatography A 520: 339-347, November 1990), the entire disclosure of which is incorporated herein by reference. For example, the *cannabis* (or other plant material) may be maintained at approximately 225 degrees Celsius for approximately 35 to 45 minutes.

In at least one example embodiment, the dry mixture can also include tobacco material (in addition to or in lieu of the *cannabis* material and/or cellulose). In at least one other example embodiment, the filling material 104 includes tobacco plant material in an amount less than or equal to about 5 weight percent (e.g., less than or equal to about 4 weight percent, less than or equal to about 3 weight percent, less than or equal to about 2 weight percent, or less than or equal to about 1 weight percent). In at least one other example embodiment, the filling material 104 is free of tobacco plant material.

In at least one example embodiment, the filling material 104 includes one or more additives. The additives may include one or more mouth-soluble polymers, partially-soluble fibers (e.g., sugar beet fibers), one or more plasticizers, one or more energizing agents, one or more focusing agents (e.g., gingko biloba), one or more alkaloids, one or more minerals, one or more vitamins, one or more dietary supplements, one or more nutraceuticals, one or more coloring agents, one or more amino acids, one or more sensates or chemesthetic agents, one or more soothing agents, one or more botanicals (e.g., green tea), one or more tooth-whitening agents (e.g., sodium hexametaphosphate (SHMP)), a therapeutic agent, a processing aid, a stearate (e.g., magnesium and/or potassium), one or more waxes (e.g., glycerol monostearate, propylene glycol monostearate, and/or an acetylated monoglyceride), one or more lubricants (e.g., sodium lauryl sulfate (SLS)), one or more preservatives (e.g., sodium benzoate), one or more fillers, one or more effervescent agents (e.g., carbon dioxide embedded in a flavor or the filling material 104), or any combination thereof. The oral pouch product may include multiple additional elements. Additionally, a single element may belong to more than one of the categories above. In at least one example embodiment, the filling material 104 includes the one or more additives in an amount greater than or equal to about 0.01 weight percent (e.g., greater than or equal to about 0.5 weight percent, greater than or equal to about 1 weight percent, greater than or equal to about 5 weight percent, greater than or equal to about 10 weight percent, greater than or equal to about 15 weight percent, greater than or equal to about 20 weight percent, or greater than or equal to about 25 weight percent). The filling material 104 may include the one or more additives in an amount less than or equal to about 30 weight percent (e.g., less than or equal to about 25 weight percent, less than or equal to about 20 weight percent, less than or equal to about 15 weight percent, less than or equal to about 10 weight percent, less than or equal to about 5 weight percent, less than or equal to about 1 weight percent, or less than or equal to about 0.5 weight percent).

In at least one embodiment, the one or more materials disposed in the inner cavity 106 as the filling material 104, including, for example only, the one or more additives and/or one or more functional ingredients, may be provided in the form of a plurality of capsules, microcapsules, and/or beads of various sizes. The capsules, microcapsules, and/or beads may have a size that is determined by the desired size of the final product (e.g., oral pouch product 100). For example, the capsules, microcapsules, and/or beads may range in size from about 0.1 mm to about 8 mm depending on the ingredients contained therein.

In each instance, each capsule, microcapsule, and/or bead may include an outer shell and an inner core. Varying the thicknesses of the outer shells of the capsules, microcapsules, and/or beads included can allow for the ingredients contained in each of the capsules, microcapsules, and/or beads to be released at varying rates to prolong the flavor and/or functional experience of the oral pouch product 100. In some example embodiments, the shells range in thickness from about 0.1 mm to about 7 mm, depending on the size of the capsules, microcapsules, and/or beads and a desired dissolution rate. The capsules, microcapsules, and/or beads having the thinnest shells dissolve first to release the enclosed flavors and functional ingredients. Capsules, microcapsules, and/or beads having thicker shells dissolve at a slower rate to provide continued flavor and functional ingredients.

In at least one example embodiment, one or more materials in the filling material 104 may be provided as granules, such as encapsulated nicotine granules and/or encapsulated sweetener granules, as described in U.S. patent application Ser. No. 17/223,773, the entire contents of which is incorporated herein by reference.

In at least one example embodiment, the additives include one or more mouth-soluble polymers. As used herein, "mouth-soluble" means that the polymer experiences significant degradation when exposed to saliva within an oral cavity over a period of about four hours. In at least one example embodiment, the mouth-soluble polymer disintegrates when exposed to saliva at the normal human body temperature for a period of less than or equal to about an hour (e.g., less than or equal to about 30 minutes, less than or equal to about 15 minutes, less than or equal to about 10 minutes, or less than or equal to about 5 minutes). The mouth-soluble polymer may be biocompatible.

In at least one example embodiment, the mouth-soluble polymer may include a cellulosic polymer, such as carboxymethyl cellulose ("CMC"), hydroxypropyl cellulose ("HPC"), hydroxyethyl cellulose ("HEC"), hydroxypropyl methyl cellulose ("HPMC"), and/or methyl cellulose ("MC"); a natural polymer, such as a starch, a modified starch, konjac, collagen, inulin, soy protein, whey protein, casein, and/or wheat gluten; a seaweed-derived polymer, such as a carrageenan (e.g., kappa carrageenan, iota carrageenan, lambda carrageenan), an alginate (e.g., propylene glycol alginate); a microbial-derived polymer, such as xanthan, dextran, pullulan, curdlan, and/or gellan; an extract, such as locust bean gum, guar gum, tara gum, gum tragacanth, pectin (e.g., low methoxy and amidated), agar, zein, karaya, gelatin, psyllium seed, chitin, and/or chitosan, an exudates, such as gum acacia (arabic) and/or shellac; a synthetic polymer, such as polyvinyl pyrrolidone, polyethylene oxide, and/or polyvinyl alcohol, or any combination thereof. Other useful mouth-soluble polymers are known in the art, for example, see Krochta et al. Food Technology, 1997, 51:61-74, Glicksman Food Hydrocolloids CRC 1982, Krochta Edible Coatings and Films to Improve Food Quality Technomic 1994, Industrial Gums Academic 1993, Nussinovitch Water-Soluble Polymer Applications in Foods Blackwell Science 2003, the entire contents of which are incorporated herein by reference.

In at least one example embodiment, the filling material 104 includes a plasticizer. The plasticizer may include one or more triglycerides (e.g., long, medium, and/or short chain), triacetin, propylene glycol, glycerin, vegetable oil, a phthalate, one or more esters of a polycarboxylic acid with a linear or branched aliphatic alcohol of moderate chain length, or any combination thereof. The plasticizer may be present in addition to triglycerides and/or other oils in the liquid mixture.

In at least one example embodiment, the filling material 104 includes one or more energizing agents. In at least one example embodiment, the energizing agent includes caffeine, taurine, glucaronalactone, guarana, vitamin B6, vitamin B12, and the like. Caffeine may include synthetic caffeine and/or natural caffeine, such as coffee-bean-extracted caffeine. In at least one example embodiment, the oral pouch product includes caffeine in an amount greater than or equal to about 10 mg (e.g., greater than or equal to about 25 mg, greater than or equal to about 50 mg, greater than or equal to about 75 mg, greater than or equal to about 100 mg, greater than or equal to about 150 mg) The caffeine may be included in an amount less than or equal to about 200 mg (e.g., less than or equal to about 150 mg, less than or equal to about 100 mg, less than or equal to about 75 mg, less than or equal to about 50 mg, or less than or equal to about 25 mg).

In at least one example embodiment, the filling material 104 includes a filler. The filler may be configured to alter a texture or pliability of the oral pouch product 100 compared to an oral pouch product without the filler. The filler may include mouth-soluble elements, mouth-insoluble elements, or both mouth-soluble and mouth-insoluble elements. Mouth-soluble elements may be configured to dissolve or disintegrate when in an adult consumer's mouth to render the oral pouch product more pliable. Fillers may include dicalcium phosphate, calcium sulfate, one or more clays, silica, glass particles, glyceryl palmitostearate, sodium stearyl fumarate, talc, or any combination thereof. Additionally, certain elements described above may also be classified as fillers, such as mouth-soluble fibers, sweeteners, minerals, or any combination thereof. In at least one example embodiment, cellulosic materials may be present in the oral pouch product 100 as fillers in addition to or as an alternative to being carriers for the liquid mixture.

The at least one sensate or chemesthesis agent may include mint, menthol, cinnamon, pepper, jambu, or any combination thereof. In certain embodiments, the at least one sensate or chemesthesis agent may include any soothing, cooling, and/or warming agent. For example, the at least one sensate or chemesthesis agent may include capsaicin, pipeline, alpha-hydroxy-sanshool, and (8)-gingerole, which may be selected to provide a warm, tingling or burning sensation. In other example embodiments, the at least one sensate or chemesthesis agent may include menthol, menthyl lactate, WS-3 (N-Ethyl-p-menthane-3-carboxamide), WS-23 (2-Isopropyl-N,2,3-trimethylbutyramide) and Evercool 180™ (available from Givaudan SA), which may be selected to provide a cooling sensation.

The at least one soothing agent may include, for example only, chamomile, lavender, jasmine, theanine, melatonin, soursop, cannabidiol, or any combination thereof.

In at least one example embodiment, the pouch wrapper 102 includes an outer web 108. The outer web 108 may be formed from a material that is generally recognized as safe ("GRAS") for use and/or contact with food. The material may be stain resistant, water permeable, and/or porous. The outer web 108 may have a thickness of about 0.05 mm to about 0.25 mm (e.g., about 0.075 mm to about 0.100 mm or about 0.1 mm to about 0.20 mm). The outer web 108 can be formed of a permeable material or a semi-permeable material, such that, for example, saliva, water, or both saliva and water can pass through the outer web 108 and into the inner cavity 406 defined by the pouch wrapper 102. Flavors and juices formed by mixing of the saliva and/or water with the filling material 104 contained within the oral pouch product 100 can be drawn out of the oral pouch product 100 through the outer web 108.

In at least one example embodiment, the wrapper 102 includes a non-woven material. The non-woven material may be formed of a polymer, including one or more synthetic and/or natural polymers. For example, wrapper 102 may be formed of a mesh material formed of spun or melt-blown fibers, such as polyurethane fibers as described in U.S. Pat. Nos. 10,448,669, 10,463,070, and/or 9,414,624, the entire contents of each of which is incorporated herein by reference thereto. The mesh material may be at least partially elastomeric. The mesh material may be white and may exclude any colorant. In other example embodiments, the mesh material may include a colorant. Further, because of the material used to form the wrapper 102, the oral pouch product 100 may exclude seams so as to provide a softer pouch.

In at least one example embodiment, the mesh material has a basis weight of greater than or equal to about 10 grams per square meter ("gsm") (e.g., greater than or equal to about 15 gsm, greater than or equal to about 20 gsm, greater than or equal to about 25 gsm, greater than or equal to about 30 gsm, greater than or equal to about 35 gsm, greater than or equal to about 40 gsm, or greater than or equal to about 45 gsm). The basis weight may be less than or equal to about 50 gsm (e.g., less than or equal to about 45 gsm, less than or equal to about 40 gsm, less than or equal to about 35 gsm, less than or equal to about 30 gsm, less than or equal to about 25 gsm, less than or equal to about 20 gsm, or less than or equal to about 15 gsm). In at least one example embodiment, the basis weight ranges from about 20 gsm to about 30 gsm.

In at least one other example embodiment, the outer web 108 comprises a paper. For example, the outer web 108 can be formed of a cellulose fiber material, such as tea bag material or other materials typically used to form snus pouches. In at least one example embodiment, the outer web 408 has a desired (or alternatively, predetermined) level for basis weight and/or wet strength to reduce occurrence of breakage of the pouch wrapper 102 during manufacturing operations, storage, and placement in an adult consumer's mouth. For example, the outer web 108 may comprise a tea bag material having a basis weight of about 16.5 gsm with a wet tensile CD strength of 68 N/m. In another example embodiment, the outer web 108 may be formed of a paper having a wet MD tensile strength of about 45 N/mm to about 52 N/mm.

In at least one example embodiment, the outer web 108 is formed of a hydrophobic paper or material. The hydrophobic paper may be formed of a cellulosic material. The hydrophobic paper may be non-woven material and may include any hydrophobic materials. The hydrophobic materials may be synthetic materials and/or semi-synthetic materials. The hydrophobic materials may include viscose, rayon, lyocell, and/or modal fibers. The outer web 108 may be treated to make the outer web 108 hydrophobic. In other example embodiments, the hydrophobic material may be a woven material.

In at least one example embodiment, the wrapper 102 is free of an added coloring agent. In at least one example embodiment, the wrapper 102 is white due to a natural color of the polymer(s) used to form the wrapper. However, in other example embodiments, the wrapper 102 may be colored to indicate a flavor of the filling material 404 contained therein. The color of the wrapper 102 may be selected to identify contents thereof. For example, a green pouch wrapper may be used to identify an oral pouch product including a mint flavorant, while a red pouch wrapper may be used to identify an oral pouch product including cinnamon.

The material used to form the outer web 108 may have a neutral or pleasant taste and/or aroma. In at least one example embodiment, the outer web 108 may be impregnated or coated with at least one flavorant, at least one *cannabis* material, at least one tobacco material, at least one binder, at least one sensate or chemesthesis agent, at least one functional ingredient, at least one salivation inducing ingredient, or any combination thereof to enhance a flavor of the filling material 104 contained within the oral pouch product 100. A substantially continuous coating including the at least one flavorant and/or the at least one *cannabis* material and/or at least one tobacco material and/or the at least one binder and/or the at least one sensate or chemesthesis agent may be coated on outer (exterior facing) surfaces of the outer web 108. In at least one example embodiment, the coating may be formed on only a portion of the outer web 108, such as only along the seams or only on one side of the oral pouch product 100. The coating can provide an initial flavor burst upon placement of the oral pouch product 100 in an oral cavity, while the inner filling material 104 provides a later flavor release to prolong flavor release during placement in an adult consumer's mouth.

The at least one flavorant may be any flavorant disclosed herein for inclusion in the filling material 104. In at least one example embodiment, the at least one flavorant may be coated on or impregnated in the outer web 408 in an amount ranging from about 0.01 weight percent to about weight percent based on the weight of the oral pouch product 100 (e.g., about 0.1 weight percent to about 4.5 weight percent, about 1 weight percent to about 4 weight percent, about 1.5 weight percent to about 3.5 weight percent, about 2 weight percent to about 3 weight percent).

In at least one example embodiment, the at least one *cannabis* or tobacco material may be coated on or impregnated in the outer web 108. The at least one *cannabis* or tobacco material may include, for example only, a ground *cannabis* or tobacco material, *cannabis* or tobacco plant fibers, and/or any extract thereof. The at least one *cannabis* or tobacco material may be coated on or impregnated in the outer web 108 in an amount ranging from about 0.01 weight percent to about 5 weight percent based on the weight of oral pouch product 100 (e.g., about 0.1 weight percent to about 4.5 weight percent, about 1 weight percent to about 4 weight percent, about 1.5 weight percent to about 3.5 weight percent, or about 2 weight percent to about 3 weight percent).

In at least one example embodiment, the at least one binder may be coated on or impregnated in the outer web 108. The at least one binder is a food grade adhesive, gum, or other binder. For example, in some example embodiments, the at least one binder includes, without limitation, sodium alginate, sugar, agar, guar gum, and the like. The at least one binder may be coated on or impregnated in the outer web in an amount ranging from about 0.01 weight percent to about 5 weight percent based on the weight of the oral pouch product 100 (e.g., about 0.1 weight percent to about 4.5 weight percent, about 1 weight percent to about 4 weight percent, about 1.5 weight percent to about 3.5 weight percent, about 2 weight percent to about 3 weight percent).

The at least one sensate or chemesthesis agent may be any of those discussed above with respect to the filling material 104. The at least one sensate or chemesthesis agent may be coated on or impregnated in the outer web 108 in an amount ranging from about 0.01 weight percent to about 5 weight percent based on the weight of the oral pouch product 100 (e.g., about 0.1 weight percent to about 4.5 weight percent, about 1 weight percent to about 4 weight percent, about 1.5 weight percent to about 3.5 weight percent, or about 2 weight percent to about 3 weight percent).

In at least one example embodiment, the at least one functional ingredient may include an antioxidant, a soothing agent, an energizing agent, an effervescent, or any combination thereof, such as those described above in the discussion of the filling material 104. In at least one example embodiment, the at least one functional ingredient may be coated on or impregnated in the outer web 108 in an amount ranging from about 0.01 weight percent to about 5 weight percent based on the weight of the oral pouch product 100 (e.g., about 0.1 weight percent to about 4.5 weight percent, about 1 weight percent to about 4 weight percent, about 1.5 weight percent to about 3.5 weight percent, or about 2 weight percent to about 3 weight percent).

The oral pouch product 100 may be an oral pouch product having, for example only, a generally rectangular shape, a ravioli or pillow shape, an oblong shape, or any other suitable shape. Various shapes may be utilized so long as the shapes fit comfortably and discreetly in an adult consumer's mouth. In at least one example embodiment, the oral pouch product 100 is substantially free of oral cavity irritant, which, as used herein, means that the shape, configuration, and position of the oral pouch product 100 do not irritate oral tissues (e.g., gums) via sharp edges and the like. Furthermore, "substantial" and "substantially free" as used in connection with oral cavity irritant means that the shape, configuration, and position of the oral pouch product 100 does not irritate oral tissues (e.g., gums) in a time frame or period having the same order of magnitude as a typical length of time during which the oral pouch product 100 may be enjoyed by an adult consumer. Generally, sharp corners are avoided as sharp corners may lead to oral discomfort.

The oral pouch product 100 may be sized and configured to fit comfortably in an adult consumer's mouth, such as between the cheek and gum. In at least one example embodiment, the oral pouch product 100 has a major dimension in the range of about 0.20 inch to about 2.0 inches (e.g., about 0.25 inch to 1.75 inches, about 0.75 inch to about 1.5 inch) and a transverse dimension in the range of about 0.25 to about 1.5 inches (e.g., about 0.50 inch to 1.25 inches, about 0.75 inch to about 1.0 inch). The oral pouch product 100 may weigh about 0.25 gram (g) to about 2.0 grams (e.g., about 0.3 gram to about 1.8 grams, about 0.4 gram to about 1.5 grams, about 0.5 gram to about 1.25 grams, or about 0.75 gram to about 1.0 gram).

The oral pouch product 100 may be placed in an adult consumer's mouth for about 1 minute to about 3 hours (e.g., about 1 minute to about 2 hours, about 5 minutes to about 90 minutes, about 10 minutes to about 60 minutes, about 20 minutes to about 40 minutes). The size of the oral pouch product 100 may be selected based on desired length of placement in an adult consumer's mouth. For example, a larger pouch including a larger amount of filling material may provide for longer placement. In at least one example embodiment, the oral pouch product 100 is discarded after a single placement in an adult consumer's mouth.

FIG. 2A is a perspective view of an oral pouch product according to at least one example embodiment.

Figure 2C:
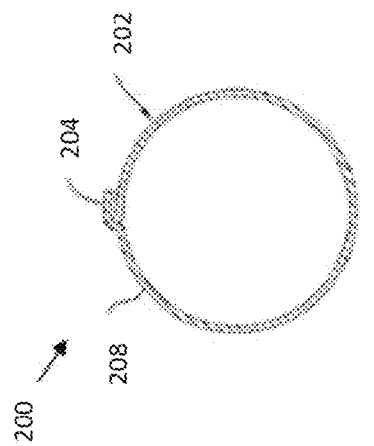
FIG. 2C is a cross-sectional view of the oral pouch product along line III-III of FIG. 2A according to at least one example embodiment.
Figure 2B:
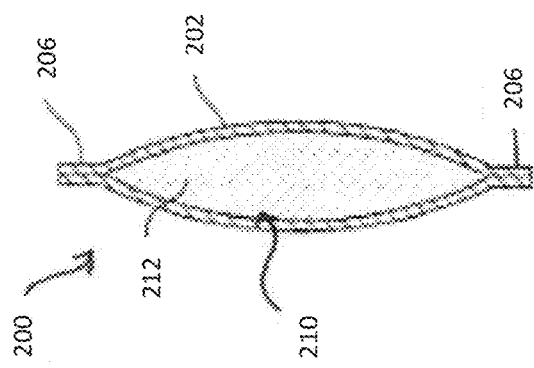
FIG. 2B is a cross-sectional view of the oral pouch product along line II-II of FIG. 2A according to at least one example embodiment.

FIG. 2B is a cross-sectional view of the oral pouch product along line II-II of FIG. 2A according to at least one example embodiment.

FIG. 2C is a cross-sectional view of the oral pouch product along line III-III of FIG. 2A according to at least one example embodiment.

In at least one example embodiment, as shown in FIGS. 2A-2C, an oral pouch product 200 is the same as that of FIGS. 1A-1B except that a pouch wrapper 202 includes one or more seals or seams, such as a longitudinal seal 204 and fin seals 206. The longitudinal seal 204 extends between the fin seals 206. In at least one example embodiment, as shown in FIG. 2C, the longitudinal seal 204 may include overlapping edge portions of the outer web 208 that are sealed together. In at least one example embodiment, the seals 204, 206 may have a dimension of less than about 1 mm. The sealing function can be accomplished by a food grade adhesive or by mutually sealing the overlapping edge portions, using thermal or sonic techniques.

In at least one example embodiment, as shown in FIG. 2B, opposing layers of an outer web 208, the longitudinal seal 204, and the fin seals 206 define an inner cavity 210 therebetween. A filling material 212, which may be the same as that of FIGS. 1A-1B, may be held within the inner cavity 210. In at least one example embodiment, the filling material 212 completely fills the interior cavity 210 of the oral pouch product 200. In other example embodiments, the filling material 210 only partially fills the interior cavity 210 of the oral pouch product 200.

As illustrated in FIG. 2B, each fin seal 206 is formed by bringing together an inner surface of the outer web 208 of the pouch wrapper 202 and another section of the inner surface of the outer web 208 in a superposed relation to form one of the fin seal. The fin seal can then be sealed using any method such as detailed above to form the fin seal 206. Though not illustrated, in certain embodiments, integrated fin and longitudinal seals may be used, as would be recognized by the skilled artisan. By overlapping a fin seal, the oral pouch product 200 may be made more comfortable for insertion in the adult consumer's mouth because there are no loose, unsealed edges that may stick out and snag the consumer's mouth during enjoyment. In addition, integrated fin and longitudinal seals may be stronger to reduce and/or prevent breakage during manufacture, packaging, shipment, placement, and/or use of the oral pouch product 200.

Figure 3B:
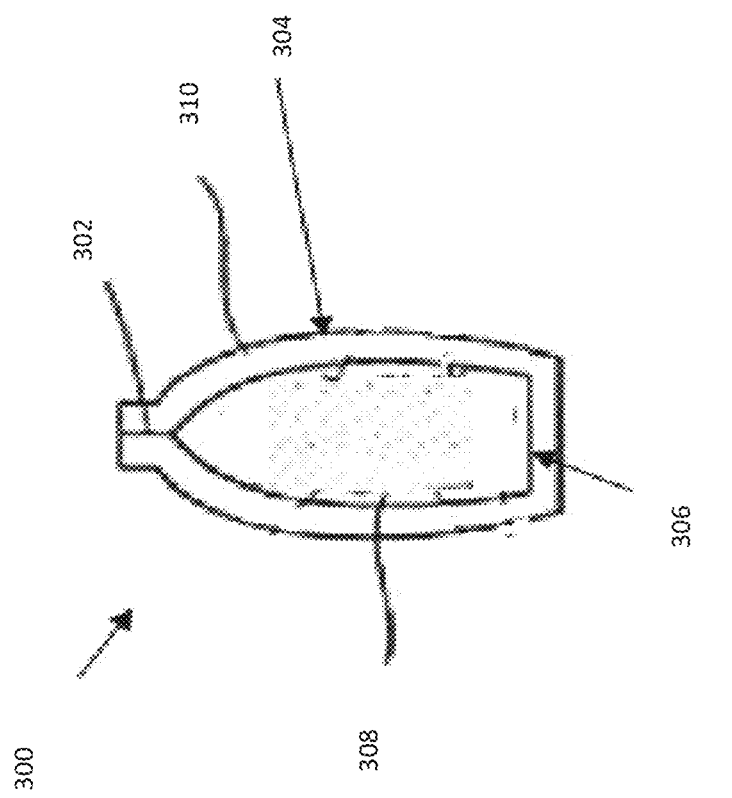
FIG. 3B is a cross-sectional view along line VII-VII of the oral pouch product of FIG. 3A according at least one example embodiment.
Figure 3A:
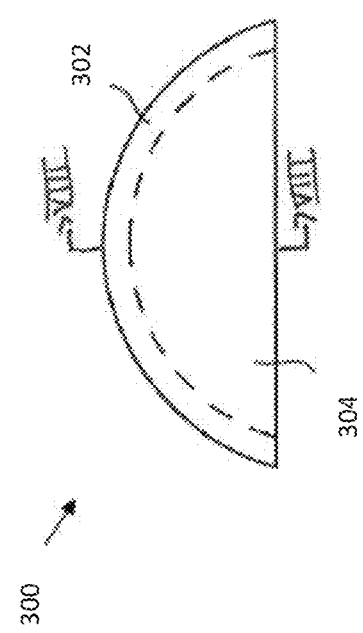
FIG. 3A is a side view of an oral pouch product according to at least one example embodiment.

FIG. 3A is a side view of an oral pouch product according to at least one example embodiment.

FIG. 3B is a cross-sectional view along line VII-VII of the oral pouch product of FIG. 3A according at least one example embodiment.

In at least one example embodiment, as shown in FIGS. 3A-3B, an oral pouch product 300 is the same as that of FIGS. 1A-1B except that the oral pouch product 300 has a single seam or seal 302 along a pouch wrapper 304. In at least one example embodiment, as shown, the oral pouch product 300 has a half moon shape. In some example embodiments, the pouch oral pouch product 300 has a D-shape, boomerang, crescent, or other shape.

In at least one example embodiment, the pouch wrapper 304 can be sealed along the seam or seal 302 to define an inner cavity 306 that is configured to contain or hold the filling material 308, which is the same as described with respect to FIGS. 1A-1B. The single seam or seal 302 can be formed by bringing together an inner surface of an outer web 310 of the pouch wrapper 304 and another section of the inner surface of the outer web 310 in a superposed relation. The sealing function can be accomplished by a food grade adhesive or by mutual sealing the adjacent portions, using thermal or sonic techniques.

Liquid Mixtures of Oil and Liquid Nicotine

In at least one example embodiment, the oral pouch product of FIGS>1-3 includes a liquid mixture including oil and nicotine as described below.

Figure 4C:
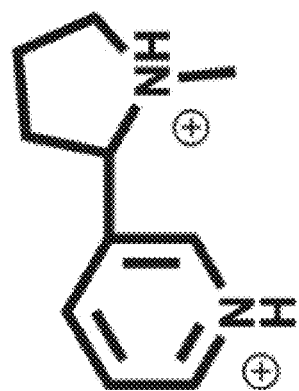
FIG. 4C is a chemical structure of di-protonated nicotine.
Figure 4B:
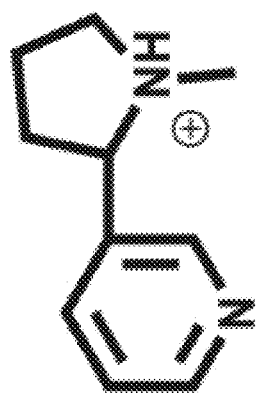
FIG. 4B is a chemical structure of mono-protonated nicotine.
Figure 4A:
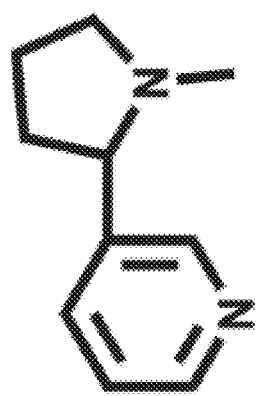
FIG. 4A is a chemical structure of free-base nicotine.

FIGS. 4A-4C depict chemical structures of nicotine in different forms.

Nicotine, or 3-(1-methyl-2-pyrrolidinyl) pyridine, is a tertiary amine. Under ambient conditions, nicotine is an oily, volatile, hygroscopic liquid. In this state, nicotine is a free base (non-protonated) and has the structure as shown in FIG. 4A. Free-base nicotine has a $pK_a$ value of about 8.

Nicotine may also be in a form of a complex or a salt. Nicotine complexes and salts may be provided in solid form, such as a powder. One example of a nicotine complex that is used in oral pouch products is nicotine polacrilex. In a salt, nicotine is mono-protonated, as shown in FIG. 4B, or di-protonated, as shown in FIG. 4C. Mono-protonated and di-protonated nicotine have lower $pK_a$ values than free-base nicotine. Nicotine salts may include nitrate, monotartrate, bitartrate, bitartrate dihydrate, salicylate, sulfate or bisulfate, phosphate or acid phosphate, acetate, lactate, succinate, maleate, fumarate, gluconate, saccharate, benzoate, methanesulfonate, hydrochloride, hydrobromide, hydroiodide, or any combination thereof.

Oral pouch products, such as those described with respect to FIGS. 1-3, often include nicotine in the form of a complex or salt for reasons related to manufacturing, handling, and stability. However, nicotine is believed to more readily absorb in the buccal mucosa at higher $pK_a$ values. Accordingly, oral pouch products including nicotine in a protonated state may also include a pH adjuster to create a more basic environment in the oral pouch product.

In at least one example embodiment, an oral pouch product includes a liquid mixture of nicotine and an oil. The oil may include one or more triglycerides, one or more diglycerides, one or more monoglycerides, triacetin, triolein, trilinolein, vegetable oil, one or more partially-hydrogenated oils, or any combination thereof. The triglyceride may include one or more short-chain triglycerides ("SCT"), one or more medium chain triglycerides ("MCT"), one or more long chain triglycerides ("LCT"), or any combination thereof.

An oral pouch product including the liquid mixture may be configured to have increased buccal nicotine absorption compared to oral pouch products including aqueous nicotine, nicotine complexes, and/or nicotine salts. The nicotine may be liquid nicotine. At least a portion of the liquid nicotine may be dissolved in the oil to form a solution of the oil and the liquid nicotine. In at least one example embodiment, all of the liquid nicotine is dissolved in the oil. In at least one example embodiment, the liquid mixture may consist essentially of liquid nicotine and an oil (e.g., triglyceride, such as a medium-chain triglyceride (MCT)).

A weight ratio of the oil to (e.g., triglyceride) the nicotine in the liquid mixture may be greater than or equal to about 1:1 (e.g., greater than or equal to about 3:2, greater than or equal to about 2:1, greater than or equal to about 3:1, greater than or equal to about 4:1, greater than or equal to about 5:1, greater than or equal to about 6:1, greater than or equal to about 7:1, greater than or equal to about 8:1, greater than or equal to about 9:1, or greater than or equal to about 10:1). The weight ratio may be less than or equal to about 95:5 (e.g., less than or equal to about 9:1, less than or equal to about 8:1, less than or equal to about 7:1, less than or equal to about 6:1, less than or equal to about 5:1, less than or equal to about 4:1, less than or equal to about 3:1, or less than or equal to about 3:2). In at least one example embodiment, the weight ratio ranges from about 1:1 to about 9:1 (e.g., from about 3:2 to about 4:1, from about 3:1 to about 5:1, or about 4:1).

In at least one example embodiment, the oral pouch product may include additional oil beyond what is present in the liquid mixture. The additional oil may, in at least one example embodiment, be used as a plasticizer. A ratio of the oil to the liquid nicotine in the oral pouch product (i.e., both the liquid mixture and any additional oil) may be greater than or equal to about 1:1 (e.g., greater than or equal to about 3:2, greater than or equal to about 2:1, greater than or equal to about 3:1, greater than or equal to about 4:1, greater than or equal to about 5:1, greater than or equal to about 6:1, greater than or equal to about 7:1, greater than or equal to about 8:1, greater than or equal to about 9:1, greater than or equal to about 10:1, greater than or equal to about 15:1, greater than or equal to about 20:1, greater than or equal to about 25:1, greater than or equal to about 30:1, greater than or equal to about 40:1, greater than or equal to about 50:1, greater than or equal to about 60:1, greater than or equal to about 70:1, greater than or equal to about 75:1, or greater than or equal to about 80:1). The weight ratio of the oil to the liquid nicotine may be less than or equal to about 100:1 (e.g., less than or equal to about 90:1, less than or equal to about 80:1, less than or equal to about 75:1, less than or equal to about 70:1, less than or equal to about 60:1, less than or equal to about 50:1, less than or equal to about 40:1, less than or equal to about 30:1, less than or equal to about 25:1, less than or equal to about 20:1, less than or equal to about 15:1, less than or equal to about 10:1, less than or equal to about 9:1, less than or equal to about 8:1, less than or equal to about 7:1, less than or equal to about 6:1, less than or equal to about 5:1, less than or equal to about 4:1, less than or equal to about 3:1, less than or equal to about 2:1, or less than or equal to about 3:2).

Figure 5A:
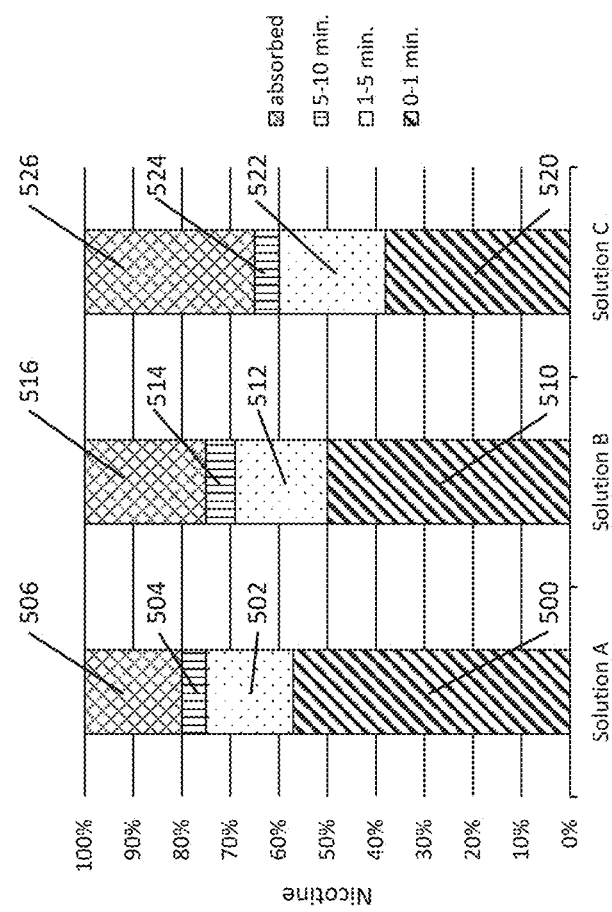
FIGS. 5A-5B are a graphs depicting buccal nicotine disposition for different nicotine solutions.
Figure 5B:
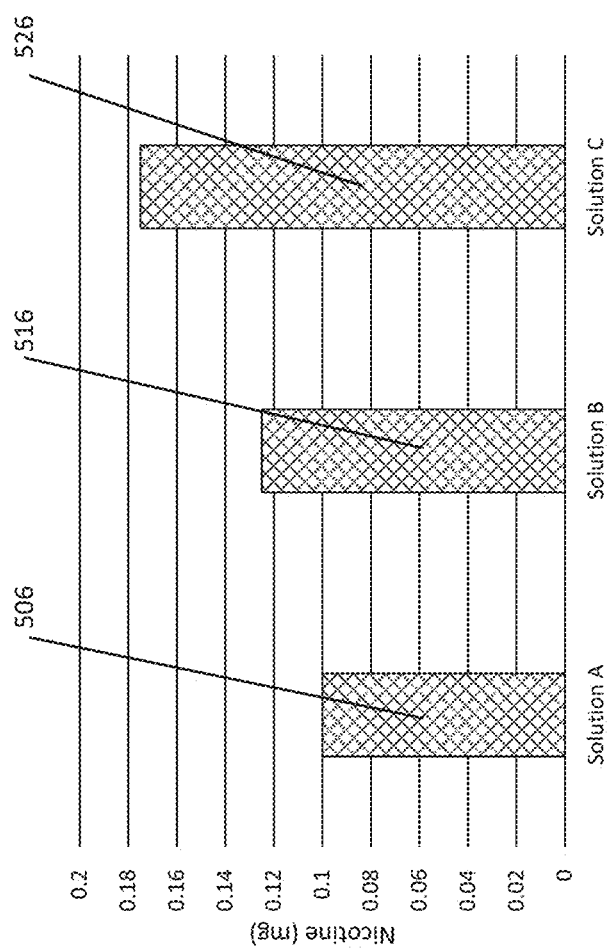

FIGS. 5A-5B are a graphs depicting buccal nicotine disposition for different nicotine solutions.

In at least one example embodiment, providing the nicotine dissolved in an oil, such as triglyceride, may facilitate increased buccal absorption compared to nicotine in an aqueous phase. It is believed that providing the nicotine dissolved in the triglyceride facilitates retention of at least a portion of the nicotine in its free-base state, regardless of the presence of a pH adjuster.

As shown in FIGS. 5A-5B, three solutions are prepared according to Table 5, below. Amounts in Table 1 are by weight percent. Solution A includes 0.5 mg liquid nicotine in water having a pH of 7. Solution B includes 0.5 mg nicotine in water having a pH of 10. Solution C includes 0.5 mg nicotine in MCT oil.

TABLE 1

Solution Compositions by Weight Percent

| | Solution A | Solution B | Solution C |
|---|---|---|---|
| Nicotine | 0.050% | 0.050% | 0.050% |
| Propylene Glycol | 0.200% | 0.200% | — |
| MCT | — | — | 99.950% |
| Water | 99.732% | 99.746% | — |
| Citric Acid | 0.018% | — | — |
| Sodium Carbonate | — | 0.004% | — |

To determine the amount of nicotine absorbed, versus the amount not absorbed, each of Solutions A, B, and C is held in an oral cavity of an adult tobacco consumer. Five adult tobacco consumers participate. Expectorant samples are collected for each of the five adult tobacco consumers for each of the three solutions at three time intervals: 0-1 minute, 1-5 minutes, and 5-10 minutes. Each expectorant sample is analyzed to measure a weight of nicotine in the expectorant sample. The nicotine measured in the expectorant samples is necessarily not absorbed in the buccal mucosa. An amount of absorbed nicotine is calculated for each solution based on a difference between a known weight of nicotine in each solution and the measured amounts of nicotine in each of the expectorant samples for each solution, as described in greater detail below.

Solution A includes 0.5 mg of nicotine. A first solution A expectorant sample 500 is collected at 0-1 minute, and includes 57 weight percent of the 0.5 mg of nicotine. A second solution A expectorant sample 502 is collected at 1-5 minutes, and includes 18 weight percent of the 0.5 mg nicotine. A third solution A expectorant sample 504 is collected at 5-10 minutes, and includes 5 weight percent of the 0.5 mg of nicotine. Accordingly, a solution A absorbed nicotine 506 is calculated to be 20 weight percent (100%–57%–18%–5%=20%).

Solution B includes 0.5 mg of nicotine. A first solution B expectorant sample 510 is collected at 0-1 minute, and includes 50 weight percent of the 0.5 mg of nicotine. A second solution B expectorant sample 512 is collected at 1-5 minutes, and includes 19 weight percent of the 0.5 mg nicotine. A third solution B expectorant sample 514 is collected at 5-10 minutes, and includes 6 weight percent of the 0.5 mg of nicotine. Accordingly, a solution B absorbed nicotine 516 is calculated to be 25 weight percent (100%–50%–19%–6%=25%).

Solution C includes 0.5 mg of nicotine. A first solution C expectorant sample 520 is collected at 0-1 minute, and includes 38 weight percent of the 0.5 mg of nicotine. A second solution C expectorant sample 522 is collected at 1-5 minutes, and includes 22 weight percent of the 0.5 mg nicotine. A third solution C expectorant sample 524 is collected at 5-10 minutes, and includes 5 weight percent of the 0.5 mg of nicotine. Accordingly, a solution C absorbed nicotine 526 is calculated to be 35 weight percent (100%–38%–22%–5%=35%).

As shown by the differences in behavior of Solution A and Solution B, increasing a pH of an aqueous solution, as in Solution B, facilitates increased buccal nicotine absorption. For example, the increased pH of the aqueous environment may facilitate retention of nicotine in the free-base phase. As shown by the differences in behavior of Solutions A/B and Solution C, providing the nicotine in the MCT facilitates, as in Solution C, increased buccal nicotine absorption compared to providing nicotine in an aqueous phase. Moreover, as shown by the differences in behavior of Solution B and Solution C, providing the nicotine in the MCT facilitates, as in Solution C, increased buccal absorption compared to an aqueous phase including a pH adjuster. As shown in FIG. 5B, the amount of absorbed nicotine for Solution C is higher than the amount absorbed for each of Solutions A and B.

Figure 6C:
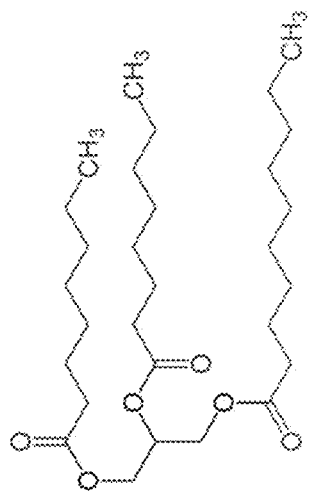
FIG. 6C depicts a chemical structure of MCT (C8-C10).
Figure 6D:
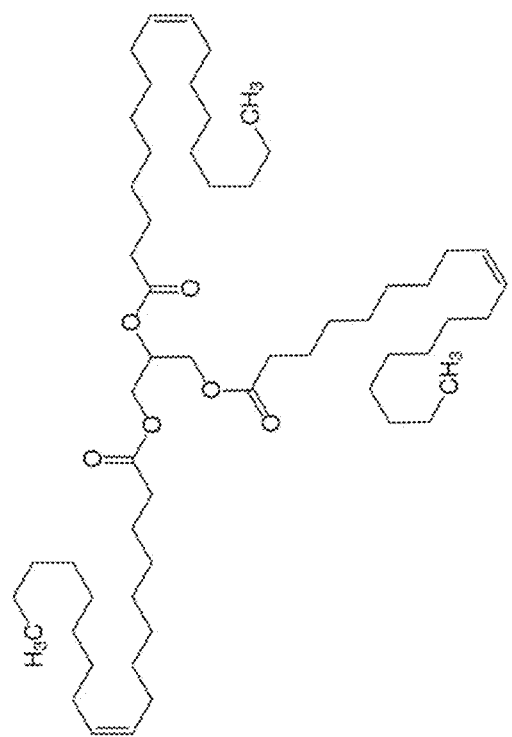
FIG. 6D depicts a chemical structure of triolein (C18).
Figure 6B:
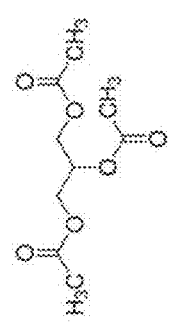
FIG. 6B depicts of a chemical structure of triacetin (C2).

FIG. 6A is a table depicting partition coefficient data for nicotine in different oil and water phase combinations. FIG. 6B depicts of a chemical structure of triacetin (C2). FIG. 6C depicts a chemical structure of MCT (C8-C10). FIG. 6D depicts a chemical structure of triolein (C18).

As shown in FIG. 6A, nicotine has solubility in both oil and water. Each of Samples 1-8 is prepared by and measured according to the following method. Liquid nicotine is added at the target nicotine concentration to a vessel containing an oil phase. The oil phase containing nicotine is mixed with an aqueous phase at a one-to-one volume ratio (v:v) using an orbital shaker at about 100 rotations per minute (rpm) for about 5 minutes to prepare a nicotine oil:aqueous phase mix. The nicotine oil:aqueous phase mix is allowed to sit at room temperature (about 25° C.) for about 24 hours. A concentration of nicotine in each of the oil phase and the nicotine phase is measured using a liquid chromatography method. A partition coefficient, which is a ratio concentrations of a compound (i.e., nicotine) in two immiscible solvents (i.e., an oil phase and an aqueous phase) at equilibrium, is calculated for each sample. The partition coefficient is a comparison of the solubilities of the nicotine in the two liquid phases.

Samples 1-6 include MCT oil (CAS No. 73398-61-5) as an oil phase. Sample 7 includes triacetin oil as an oil phase. Sample 8 includes triolein oil as an oil phase. Sample 1 includes deionized (DI) water as an aqueous phase. Sample 2 includes basified DI water having a pH of 7.4 as an aqueous phase. Sample 3 includes artificial saliva having a pH of 6.8 as an aqueous phase. Artificial saliva simulates mucus conditions. Sample 4 includes acidified DI water having a pH of 2 as an aqueous phase. Samples 5-8 include 1M acetic acid pH adjuster having a pH of 2 as an aqueous phase, which simulates stomach conditions.

In each of Samples 5-8, a partition coefficient is less than 1, indicating a higher solubility of nicotine in the acetic acid pH adjuster than the respective oil phase. This is believed to be caused by protonation of the nicotine and higher electrostatic interactions. In each of Samples 1-4, a partition coefficient is greater than 1, indicating a higher solubility in the MCT oil than the respective aqueous phase. However, in every sample, at least a portion of the nicotine is dissolved in the aqueous phase. Accordingly, if water is present in a liquid mixture, at least a portion of the nicotine will be dissolved in the water phase.

In at least one example embodiment, the oral pouch product includes water. The oral pouch product may include water in an amount less than or equal to about 10 weight percent (e.g., less than or equal to about 8 percent, less than or equal to about 5 weight percent, less than or equal to about 3 weight percent, less than or equal to about 2 weight percent, less than or equal to about 1 weight percent, less than or equal to about 0.5 weight percent. In at least one example embodiment, the oral pouch product is free of water.

In at least one example embodiment, the liquid mixture includes water in amount less than or equal to about 5 weight percent (e.g., less than or equal to about 4 weight percent, less than or equal to about 3 weight percent, less than or equal to about 2 weight percent, less than or equal to about 1 weight percent, less than or equal to about 0.5 weight percent, or less than or equal to about 0.25 weight percent). In at least one example embodiment, no water is intentionally added to the liquid mixture. However, a small amount of water may come into contact with the liquid mixture via other elements in the oral pouch product. In at least one example embodiment, the liquid mixture is free of water. Limiting an amount of water and/or omitting water may facilitate increasing an amount of nicotine dissolved in the triglyceride. Accordingly, an oral pouch product having the liquid mixture may be configured to facilitate increased buccal absorption of nicotine compared to an oral pouch product having all or a portion of the nicotine in a water phase.

As noted above, in at least one example embodiment, the nicotine may be liquid nicotine. Greater than or equal to about 50 weight percent of the nicotine may be free base nicotine (e.g., greater than or equal to about 55 weight percent, greater than or equal to about 60 weight percent, greater than or equal to about 65 weight percent, greater than or equal to about 70 weight percent, greater than or equal to about 75 weight percent, greater than or equal to about 80 weight percent, greater than or equal to about 85 weight percent, greater than or equal to about 90 weight percent, greater than or equal to about 95 weight percent, greater than or equal to about 98 weight percent, or greater than or equal to about 99 weight percent). In at least one example embodiment, greater than 80 weight percent of the nicotine is free-base nicotine. In at least one example embodiment, all of the nicotine is free-base nicotine.

In at least one example embodiment, the nicotine is tobacco-derived nicotine, synthetic nicotine, or both tobacco-derived nicotine and synthetic nicotine. In at least one example embodiment, the oral pouch product includes the nicotine in an amount greater than or equal to about 0.1 mg (e.g., greater than or equal to about 1 mg, greater than or equal to about 2 mg, greater than or equal to about 4 mg, greater than or equal to about 6 mg, greater than or equal to about 8 mg, greater than or equal to about 10 mg, greater than or equal to about 12 mg). The oral pouch product may include the nicotine in an amount less than or equal to about 14 mg (e.g., less than or equal to about 12 mg, less than or equal to about 10 mg, less than or equal to about 8 mg, less than or equal to about 6 mg, less than or equal to about 4 mg, less than or equal to about 2 mg, or less than or equal to about 1 mg). In at least one example embodiment, the oral pouch product includes the liquid nicotine in an amount ranging from 0.1 mg to about 14 mg (e.g., ranging from about 2 mg to about 10 mg, ranging from about 4 mg to about 8 mg, or ranging from about 5 mg to about 6 mg).

As discussed above, the oil may include one or more monoglycerides, one or more diglycerides, one or more triglycerides, triacetin, triolein, trilinolein, vegetable oil, one or more partially-hydrogenated oils, or any combination thereof. The triglyceride may include one or more LCTs, one or more MCTs, one or more SCTs, or any combination thereof. In at least one example embodiment, the oil includes one or mores monoglyceride, one or more diglycerides, one or more triglycerides, or any combination thereof. In at least one example embodiment, the oil includes one or more triglycerides. In at least one example embodiment, the triglyceride includes MCT. In at least one example embodiment, the liquid mixture further includes triacetin, triolein, trilinolein, vegetable oil, a partially-hydrogenated oil, or any combination thereof.

In at least one example embodiment, the oral pouch product includes the oil (e.g., triglyceride) in an amount greater than or equal to about 1 weight percent (e.g., greater than or equal to about 2 weight percent, greater than or equal to about 3 weight percent, greater than or equal to about 4 weight percent, greater than or equal to about 5 weight percent, greater than or equal to about 10 weight percent, greater than or equal to about 15 weight percent, greater than or equal to about 20 weight percent, greater than or equal to about 25 weight percent, greater than or equal to about 30 weight percent, greater than or equal to about 40 weight percent, greater than or equal to about 50 weight percent, greater than or equal to about 60 weight percent, greater than or equal to about 70 weight percent, greater than or equal to about 80 weight percent, or greater than or equal to about 90 weight percent). In at least one example embodiment, the oral pouch product may include the oil (e.g., triglyceride) in an amount less than or equal to about 95 weight percent (e.g., less than or equal to about 90 weight percent, less than or equal to about 80 weight percent, less than or equal to about 70 weight percent, less than or equal to about 60 weight percent, less than or equal to about 50 weight percent, less than or equal to about 40 weight percent, less than or equal to about 30 weight percent, less than or equal to about 20 weight percent, less than or equal to about 15 weight percent, less than or equal to about 10 weight percent, less than or equal to about 7 weight percent, or less than or equal to about 5 weight percent). In at least one example embodiment, the oral pouch product includes the oil (e.g., triglyceride) in an amount ranging from 10 weight percent to 50 weight percent. In at least one example embodiment, the oral pouch product is a solid format including the oil (e.g., triglyceride) at less than or equal to about 50 weight percent.

Methods of Manufacturing an Oral Pouch Product

Figure 7:
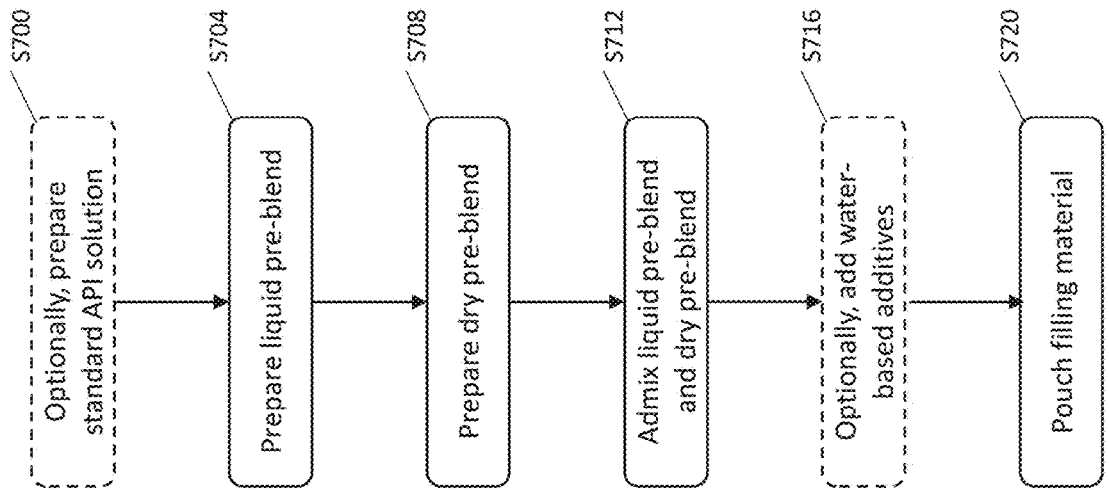
FIG. 7 is a flowchart depicting a method of preparing an oral pouch product according to at least one example embodiment.

FIG. 7 is a flowchart depicting a method of manufacturing a pouch product according to at least one example embodiment.

As shown in FIG. 7, a method of preparing a filling material may optionally include preparing a standard API solution at S700. The standard API solution may include an API, such as liquid nicotine, dissolved in oil, such as MCT, at a desired (or alternatively, predetermined) weight ratio. In at least one example embodiment, the desired weight ratio is greater than or equal to about 20:80 (1:4) (e.g., greater than or equal to about 25:75, greater than or equal to about 30:70, greater than or equal to about 35:65, greater than or equal to about 40:60 (2:3), greater than or equal to about 45:55, greater than or equal to about 50:50, greater than or equal to about 55:45, greater than or equal to about 60:40, greater than or equal to about 65:35, greater than or equal to about 70:30, or greater than or equal to about 75:25). The desired weight ratio may be less than or equal to about 80:20 (e.g., less than or equal to about 75:25, less than or equal to about 70:30, less than or equal to about 65:35, less than or equal to about 60:40, less than or equal to about 55:45, less than or equal to about 50:50, less than or equal to about 45:50, less than or equal to about 40:60, less than or equal to about 35:65, less than or equal to about 30:70, or less than or equal to about 25:75).

At S704, the method may include preparing a liquid pre-blend. In at least one example embodiment, the liquid prep-blend includes API, oil, and antioxidant. In at least one example embodiment, the liquid pre-blend may be prepared by providing the standard API solution in an amount suitable to achieve a desired API content in the pouch product (i.e., more standard API solution to prepare a higher API dose product). Additional oil may be added to the standard API solution to achieve a desired liquid content in the filling material. Antioxidant, such as liquid antioxidant, may also be added to the oil and API. An amount of antioxidant may be selected based on the amount of API.

At S708, the method may include preparing a dry pre-blend. In at least one example embodiment, preparing the dry pre-blend includes admixing the insoluble material, the water-soluble filler, the pH adjuster, dry flavorant, dry antioxidant, plant material (e.g., *cannabis* and/or tobacco plant material), the emulsifier and/or surfactant, and/or other dry additives.

At S712, the method may include admixing the liquid pre-blend and the dry pre-blend. In at least one example embodiments, one or more of water activity, pH, oven volatiles, bulk density, dissolution, flowability, and API content are monitored at one or more points in the process of preparing the oral pouch product. Admixing the liquid and dry pre-blends may include providing the liquid pre-blend in an atomized spray. The ingredients may be admixed, such as in a ribbon blender. A weight ratio of dry to liquid ingredients may be as described above in the discussion accompanying FIGS. 1A-1B.

At S716, the method may optionally include adding water-based additives. Water-based additives, such as flavorant, may be added by spraying and or pouring, optionally while admixing, such as in the ribbon blender. In at least one example embodiment, the dry pre-blend is continuous stirred while the liquid pre-blend is added at S712 and the water-based additives are added at S716.

At S720, the method may include pouching the filling material. Pouching the filling material may generally include forming a wrapper into an open pouch using a vertical or horizontal fill machine and filling the open pouch with the filling material. The pouch may then be sealed to contain the filling material and form the oral pouch product. In at least one example embodiment, a series of oral pouch product are formed with a space between seals of adjacent pouch products and then cut apart to form individual pouch products. For instance, the oral pouch product may be cut with a die at a location between adjacent seals to form a soft edge on each pouch product. Alternatively, a first strip of pouch wrapper material can be advanced along a feed path, filling material can be placed on the strip, a second strip can be placed over the first strip, a sealing die can be used to press the strips together and form a seam such as a heat seal or adhesive seal around the filling, and a cuffing die can be used to cut the first and second strips outwardly of the seam to form the soft edge.

While some example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

Although described with reference to specific examples and drawings, modifications, additions and substitutions of example embodiments may be variously made according to the description by those of ordinary skill in the art. For example, the described techniques may be performed in an order different with that of the methods described, and/or elements such as the described system, architecture, devices, circuit, and the like, may be connected or combined to be different from the above-described methods, or results may be appropriately achieved by other elements or equivalents.

We claim:

1. An oral pouch product comprising:
a wrapper defining a cavity; and
a filling material in the cavity, the filling material including,
a dry mixture including,
a cellulosic material, and
a water-soluble filler, and
a liquid mixture including,
an oil including a triglyceride, a diglyceride, a monoglyceride, or any combination thereof, and
liquid nicotine dissolved in the oil,
the filling material being free of water or including water in an amount less than or equal to 5 weight percent, and
the filling material either being free of propylene glycol or including propylene glycol in an amount less than or equal to 1 weight percent.

2. The oral pouch product of claim 1, wherein the filling material is free of glycerin and propylene glycol.

3. The oral pouch product of claim 1, wherein the cellulosic material includes microcrystalline cellulose (MCC).

4. The oral pouch product of claim 3, wherein the MCC includes particles having a size ranging from 100 microns to 300 microns.

5. The oral pouch product of claim 3, wherein the MCC is wood pulp-derived MCC.

6. The oral pouch product of claim 1, wherein the filling material includes the cellulosic material in an amount ranging from 10 weight percent to 70 weight percent.

7. The oral pouch product of claim 6, wherein filling material includes the cellulosic material in an amount ranging from 30 weight percent to 60 weight percent.

8. The oral pouch product of claim 1, wherein filling material includes the oil in an amount ranging from 10 weight percent to 50 weight percent.

9. The oral pouch product of claim 8, wherein the filling material includes the oil in an amount ranging from 15 weight percent to 25 weight percent.

10. The oral pouch product of claim 1, wherein the oil consists essentially of a triglyceride, a diglyceride, a monoglyceride, or any combination thereof.

11. The oral pouch product of claim 1, wherein the oil includes the triglyceride.

12. The oral pouch product of claim 11, wherein the triglyceride includes a medium chain triglyceride.

13. The oral pouch product of claim 1, wherein the filling material includes the water-soluble filler in an amount ranging from 10 weight percent to 50 weight percent.

14. The oral pouch product of claim 1, wherein the water-soluble filler includes a sugar alcohol, a sugar, a maltodextrin, a starch, a polysaccharide, or any combination thereof.

15. The oral pouch product of claim 14, wherein the water-soluble filler includes the sugar alcohol.

16. The oral pouch product of claim 15, wherein the filling material includes the sugar alcohol in an amount ranging from 15 weight percent to 25 weight percent.

17. The oral pouch product of claim 15, wherein the sugar alcohol includes xylitol.

18. The oral pouch product of claim 1, wherein the filling material further includes a pH adjuster.

19. The oral pouch product of claim 18, wherein the pH adjuster includes sodium bicarbonate.

20. The oral pouch product of claim 1, wherein the filling material further includes an antioxidant.

21. The oral pouch product of claim 20, wherein the antioxidant includes Tocopherol, or a tocopherol derivative, ascorbic acid, an ascorbic acid derivative, tert-butylhydroquinone, or any combination thereof.

22. The oral pouch product of claim 20, wherein the filling material includes the antioxidant in an amount less than 2 weight percent.

23. The oral pouch product of claim 1, wherein the filling material further includes a flavorant.

24. The oral pouch product of claim 23, wherein the filling material includes the flavorant in an amount less than 10 weight percent.

25. The oral pouch product of claim 24, wherein the filling material includes the flavorant in an amount ranging from 0.1 weight percent to 5 weight percent.

26. The oral pouch product of claim 1, wherein the filling material includes the liquid nicotine in an amount ranging from 0.1 weight percent to 10 weight percent.

27. The oral pouch product of claim 1, wherein the liquid nicotine includes tobacco-derived nicotine.

28. The oral pouch product of claim 1, wherein the liquid nicotine includes synthetic nicotine.

29. The oral pouch product of claim 1, wherein the wrapper includes an elastomer.

30. The oral pouch product of claim 29, wherein the elastomer is white.

31. The oral pouch product of claim 29, wherein the elastomer includes polyurethane.

32. The oral pouch product of claim 29, wherein the wrapper has a basis weight ranging from 20 grams per meter (gsm) to 30 gsm.

33. An oral pouch product comprising:
a wrapper defining a cavity, the wrapper including,
an elastomer; and
a filling material in the cavity, the filling material including,
a dry mixture including,
a cellulosic material, and
a water-soluble filler, and
a liquid mixture including,
an oil including a triglyceride, a diglyceride, a monoglyceride, or any combination thereof, and
liquid nicotine dissolved in the oil,
the filling material being either free of water or including water in an amount less than or equal to 5 weight percent, and
the filling material either being free of propylene glycol or including propylene glycol in an amount less than or equal to 1 weight percent.

34. An oral pouch product comprising:
a wrapper defining a cavity; and
a filling material in the cavity, the filling material including,
a dry mixture including,
a microcrystalline cellulose in an amount ranging from 10 weight percent to 70 weight percent, and
a water-soluble filler in an amount ranging from 10 weight percent to 50 weight percent, the water-soluble filler including a sugar alcohol, and
a liquid mixture including,
a triglyceride in an amount ranging from 10 weight percent to 30 weight percent, and
liquid nicotine dissolved in the triglyceride, wherein
the filling material is free of glycerin and propylene glycol, and
the filling material is either free of water or includes water in an amount less than 5 weight percent of the filling material.

35. The oral pouch product of claim 34, wherein the wrapper includes an elastomer.

36. The oral pouch product of claim 35, wherein the elastomer includes polyurethane.

37. A method of making an oral pouch product comprising:
preparing a liquid mixture including liquid nicotine and an oil, the oil including a triglyceride, a diglyceride, a monoglyceride, or any combination thereof, at least a portion of the liquid nicotine being dissolved in the oil;
preparing a dry mixture including a cellulosic material and a water-soluble filler;
forming a filling material by admixing the liquid mixture and the dry mixture; and
forming oral pouch product by enclosing the filling material in cavity defined by a wrapper
the filling material either being free of water, or including water in an amount less than or equal to 5 weight percent of the filling material, and
the filling material being free of propylene glycol, or including propylene in an amount less than or equal to 1 weight percent.

38. The oral pouch product of claim 1, wherein substantially all of the liquid nicotine is dissolved in the oil.

39. The oral pouch product of claim 1, wherein the filling material is free of water.

40. The oral pouch product of claim 1, wherein the liquid mixture consists essentially of the triglyceride and the liquid nicotine.

* * * * *